United States Patent [19]
Ruoslahti et al.

[11] Patent Number: 5,981,478
[45] Date of Patent: Nov. 9, 1999

[54] INTEGRIN-BINDING PEPTIDES

[75] Inventors: Erkki Ruoslahti, Rancho Sante Fe; Erkki Koivunen, San Diego, both of Calif.

[73] Assignee: La Jolla Cancer Research Foundation, San Diego, Calif.

[21] Appl. No.: 08/286,861

[22] Filed: Aug. 4, 1994

Related U.S. Application Data

[63] Continuation-in-part of application No. 08/158,001, Nov. 24, 1993.

[51] Int. Cl.$^6$ .............................. A61K 38/12; C07K 5/12
[52] U.S. Cl. ................................ 514/10; 514/11; 514/14; 514/15; 514/16; 530/317; 530/327; 530/328; 530/329
[58] Field of Search ................................... 530/327, 328, 530/329, 317; 514/14, 15, 16, 10, 11

[56] References Cited

U.S. PATENT DOCUMENTS

| | | | |
|---|---|---|---|
| 4,578,079 | 3/1986 | Ruoslahti et al. | 623/11 |
| 4,957,902 | 9/1990 | Grinnell | 514/17 |
| 5,091,176 | 2/1992 | Braatz et al. | 530/816 |
| 5,110,920 | 5/1992 | Erlich | 536/27 |
| 5,352,667 | 10/1994 | Lider et al. | 514/19 |
| 5,575,815 | 11/1996 | Slepian et al. | 623/1 |
| 5,627,263 | 5/1997 | Ruoslahti et al. | 530/327 |

FOREIGN PATENT DOCUMENTS

| | | |
|---|---|---|
| 503301 | 9/1992 | European Pat. Off. . |
| WO 92/01464 | 2/1992 | WIPO . |

OTHER PUBLICATIONS

Koivunen et al. J. of Biological Chem, vol. 268, No. 27, pp. 20205–20210. Sep. 25, 1993.
Caplus on STN. No. 1993:186017. Fukuoka et al. Proc. Natl. Acad. Sci. U.S.A. 89(4). pp. 1189–1193, 1992.
O'Neil et al., "Identification of Novel Peptide Antagonist for GPIIb/IIIa from a Conformationally Constrained Phage Peptide Library", Proteins: Structure, Function, and Genetics, vol. 14 509–515, 1992.
Schulz et al., "Emprirical simialrtiies between amino acid residues", in Principles and Protein Structure, Springer–Verlag, New York 1979, pp. 14–16.
Fischer et al. "Inhibition of Osteoclastic Bone Resorption in Vivo by Echistatin an 'Arginyl–Glycyl–Aspartyl' (RGD)–Containing Protien", Endocrinology, vol. 132, No. 3, pp. 1411–1413, 1993.
Brooks et al. "Requirement of Vascular Integrin Alpha V Beta 3 for Angiogenesis", Science, vol. 264, pp. 569–571, 1994.
Gehlsen et al. "Inhibition of Invitro Tumor Cell Invasion by Arg–Gly–Asp Containing Synthetic Peptides", J. of Cell Biol., vol. 106, pp. 925–930, 1988.
Humphries et al. "A Synthetic Peptide from Fibronectin Inhibits Experminetal Metastasis of Murine Melanoma Cells", Science, vol. 233, pp. 467–470, 1986.
Koivunen et al. Phage Libraties Displaying Cyclic Petides with Different Ring Sizes: Ligand Specificities of the RGD–Directed Integrins, Bio/Technology, vol. 13, pp. 265–270, 1995.
Koivunen et al., "Selection of Peptides Binding to the a5B1 Integrin form Phage Display Library." J. Biol. Chem. 268:20205–20210, Sep. 1993.
Peishoff et al., "Investigation of Conformational Specificity at GPIIb/IIIa: Evaluation of Confromationally Constrained RGD Peptides." J. Med. Chem. vol. 35, pp. 3962–3969, 1992.
Yamada, K. "Adehsive Recognition Sequences", J. of Biol. Chem., vol. 266, No. 2, pp. 12806–12812, Jul. 1991.
Rudinger, J. (1976). Peptide Hormones (ed. J.A. Parsons). University Park Press. Baltimore. pp. 1–7.
Koivunen et al., "Phage Libraries Displaying Cyclic Peptides with Different Ring Sizes: Ligand Specificities of the RGD–Directed Integrins," Bio/Technology 13:265–270 (1995).
Samanen et al., "Development of a Small RGD Peptide Fibrinogen Receptor Antagonist with Potent Antiaggregatory Activity in Vitro," J. Med. Chem. 34:3114–3125 (1991).
Skubitz et al., "Synthetic Peptides from the Carboxy–terminal Globular Domain of the A Chain of Laminin: Their Ability to Promote Cell Adhesion and Neurite Outgrowth, and Interact with Heparin and the β1 Integrin Subunit," J. Cell Biol. 115:1137–1148 (1991).

*Primary Examiner*—Cecilia J. Tsang
*Assistant Examiner*—Anish Gupta
*Attorney, Agent, or Firm*—Campbell & Flores LLP

[57] ABSTRACT

This invention is directed to novel integrin binding peptides. These peptides bind to $\alpha_v$- of $\alpha_5$-containing integrins and can exhibit high binding affinity. They contain one of the following sequence motifs: $RX_1ETX_2WX_3$ [SEQ ID NO: 1] (especially RRETAWA [SEQ ID NO: 8]); RGDGX [SEQ ID NO: 2], in which X is an amino acid with a hydrophobic, aromatic side chain; the double cyclic $CX_1CRGDCX_2C$ [SEQ ID NO: 15]; and RLD. The peptides generally exhibit their highest binding affinity when they assume a conformationally stabilized configuration. This invention also provides methods of using these peptides.

36 Claims, 7 Drawing Sheets

INTEGRIN-BINDING PEPTIDES

This application is a continuation-in-part of U.S. application Ser. No. 08/158,001, filed Nov. 24, 1993, incorporated by reference in its entirety.

This invention was made with government support under grants CA45207, CA28896 and Cancer Center Support Grant CA30199 awarded by the National Institutes of Health. The government has certain rights to this invention.

BACKGROUND OF THE INVENTION

Integrins are transmembrane $\alpha\beta$ heterodimer receptors that are expressed on a wide variety of cells. They mediate adhesion of cells to extracellular matrix ("ECM"). There are eight known $\beta$ subunits and fourteen known $\alpha$ subunits, which associate in various combinations to form at least twenty receptors with different ligand specificities. The ligands for several of the integrins are adhesive extracellular matrix (ECM) proteins such as fibronectin, vitronectin, collagens and laminin.

It is becoming increasingly clear that the ECM influences gene expression and that changes in the expression of genes encoding matrix proteins alter the composition of the ECM. Integrins appear to mediate messages from the exterior of a cell to its interior, thereby inducing changes in gene expression. In this capacity, the integrins control many medically important biological phenomena, including cell migration during development, tissue repair, cancer cell differentiation, metastasis of tumor cells, platelet aggregation, homing of immune system cells and the extension of neuronal processes to target sites.

Many integrins, including $\alpha_5\beta_1$, $\alpha_v\beta_5$, $\alpha_{IIb}\beta_3$ and $\alpha_v\beta_3$ recognize the amino acid sequence RGD (arginine-glycine-aspartic acid), which is present in fibronectin and other adhesive proteins.

Fibronectin is the only known ECM ligand for the $\alpha_5\beta_1$ integrin and the binding of fibronectin to this integrin is mediated by an RGD sequence. In contrast, the integrins $\alpha_v\beta_3$ and $\alpha_{IIb}\beta_3$, which also recognize the RGD sequence, can bind many different adhesive proteins.

The $\alpha_5\beta_1$ integrin is important in promoting the assembly of fibronectin matrix and initiating cell attachment to fibronectin. Similarly, $\alpha_v\beta_3$, $\alpha_v\beta_5$, and $\alpha_{IIb}\beta_3$ integrins are important in promoting cell attachment to vitronectin, fibrinogen, fibronectin, osteopontin and some other RGD-containing proteins. Peptides and protein fragments containing the RGD sequence can be used to modulate the activity of the RGD-recognizing integrins. The use of RGD peptides permits targeted modulation and manipulation of cell adhesion and other integrin-mediated cellular events in various medical situations, including platelet aggregation, thrombosis, wound healing, osteoporosis, tissue repair and tumor invasion. Ruoslahti, *J. Clin. Invest.*, 87:1–5 (1991).

While RGD peptides that bind to more than one of the RGD-directed integrins have been used in some of these applications, the most developed application, anti-thrombotic use, depends on peptides that are more selective for the targeted integrin. The anti-thrombotic peptides target the platelet integrin $\alpha_{IIb}\beta_3$ (e.g. Collen et al., *Thromb. Haemos.*, 71:95–102 (1994)).

Thus, a need exists for ligands that bind integrins selectively. The present invention satisfies this need and provides related advantages as well.

SUMMARY OF THE INVENTION

This invention provides peptides that bind to various integrins. This includes peptides that bind to the $\alpha_5\beta_1$ integrin and that contain the sequence RX$_1$ETX$_2$WX$_3$ [SEQ ID NO: 1] wherein X$_1$, X$_2$ and X$_3$ are any amino acid; peptides that bind $\alpha_5\beta_1$ integrin and that contain the sequence RGDGX [SEQ ID NO: 2], wherein X is an amino acid with a hydrophobic, aromatic side chain; peptides that bind to $\alpha_v\beta_3$ integrin and that contain the sequence RLD; and peptides that bind to the $\alpha_v\beta_5$ and $\alpha_v\beta_3$ integrins and that contains the sequence X$_1$X$_2$X$_3$RGDX$_4$X$_5$X$_6$ [SEQ ID NO: 3] wherein X$_1$, X$_3$, X$_4$ and X$_6$ are capable of forming a cyclizing bond and X$_2$ and X$_5$ are 1 to 5 amino acids.

According to certain embodiments of this invention, peptides containing the sequence motifs demonstrate enhanced binding affinity when they assume constrained secondary conformation as a result of, for example, cyclization.

This invention also provides methods using these peptides. A method useful for isolating an $\alpha_v$- or $\alpha_5$-containing integrin from a sample mixture involves contacting a peptide of this invention with the sample mixture under ionic conditions to allow binding of the integrin to the peptide and separating the integrin from the peptide. The integrins are useful, for example, in the evaluation of the specificity of integrin-binding pharmaceuticals, such as anti-thrombotics. Tschopp et al., *Coronary Artery Disease*, 4:809–817 (1993). A method useful for attaching cells to a substrate involving binding a peptide of the invention to a substrate and contacting the substrate with the cell is also provided. Cell culture requires proper attachment of cells. Thus, this invention also provides devices having a peptide of this invention attached to the surface of a substrate.

This invention also provides therapeutic methods and devices utilizing these peptides. A method useful for attracting cells to the surface of an implantable prosthetic involves attaching a peptide of the invention to the surface of the implantable prosthetic and can further involve implanting the prosthetic into an individual. The invention also provides devices having a peptide of the invention attached to the surface of an implantable prosthetic. Available literature shows that such devices have advantages over uncoated devices. Glass et al., *Mat Res. Soc. Symp. Proc.*, 252:331–337 (1992).

This invention is directed to patch grafts having a peptide of this invention attached to a support matrix. A method of the invention useful for promoting wound healing involves applying a patch graft of the invention to the wound.

A therapeutic method useful for inhibiting the attachment of osteoclasts to bone, and, therefore, for treating osteoporosis, involves administering to an individual a peptide of the invention that binds to the $\alpha_v\beta_3$ integrin.

Similarly, therapeutic methods useful for inhibiting angiogenesis also involve administering to an individual a peptide of the invention that binds to the $\alpha_v\beta_3$ integrin. Inhibition of angiogenesis is important, for example, in tumor therapy.

This invention also provides a therapeutic method useful for inhibiting metastasis of tumor cells expressing, for example, the $\alpha_5\beta_1$ or $\alpha_v\beta_3$ integrin involving administering to an individual a peptide of this invention that binds to these integrins.

Another embodiment of the invention is a method useful for inhibiting migration of smooth muscle cells involving administering to an individual a peptide of the invention that binds to the $\alpha_v\beta_3$ integrin.

BRIEF DESCRIPTION OF THE DRAWINGS

FIG. 11—$\alpha_5\beta_1$-mediated attachment of B2/a27 cells to fibronectin.

FIG. 12—$\alpha_v\beta_5$-mediated attachment of HT-29 cells to vitronectin.

FIG. 13—$\alpha_v\beta_3$-mediated attachment of IMR-90 cells to vitronectin. The cells that bound were determined as described herein. The results show means from duplicate wells.

DETAILED DESCRIPTION OF THE INVENTION

Figure 1:
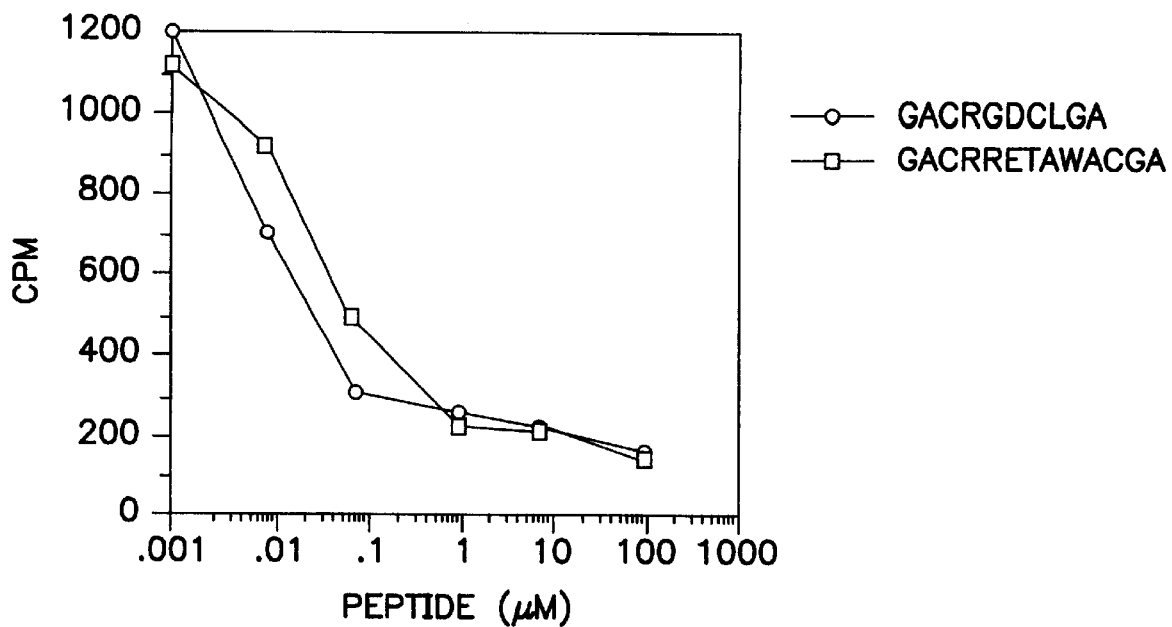
FIG. 1 shows the inhibition of $^{125}$I-fibronectin binding to $\alpha_5\beta_1$ integrin by synthetic cyclic peptides.

This invention is directed to novel integrin-binding peptides. These peptides contain one of the following amino acid sequence motifs: $RX_1ETX_2WX_3$ [SEQ ID NO: 1] (especially RRETAWA [SEQ ID NO: 8]); RGDGX [SEQ ID NO: 2], in which X is an amino acid with a hydrophobic, aromatic side chain; $X_1X_2X_3RGDX_4X_5X_6$ [SEQ ID NO: 3] and RLD.

When these peptides assume a conformationally stabilized configuration, they tend to have greater integrin-binding affinity.

The peptides of this invention have many practical uses. These uses include isolating $\alpha_5$- and $\alpha_v$-containing integrins from a mixture; promoting the attachment of cells bearing the appropriate integrin to a surface, and inhibiting the binding of such cells to macromolecules such as fibronectin, vitronectin, and osteopontin. Each of these activities is useful in various applications as detailed below.

This invention provides peptides binding to $\alpha_5\beta_1$ integrin and containing the sequence $RX_1ETX_2WX_3$ [SEQ ID NO: 1] wherein $X_1$, $X_2$ and $X_3$ are any amino acid. More particularly, this invention is directed to peptides having selectivity for $\alpha_5\beta_1$ integrin and containing the sequence $RX_1ETX_2WX_3$ [SEQ ID NO: 1] in a constrained secondary conformation. In one embodiment, the peptide contains the sequence $CRX_1ETX_2WX_3C$ [SEQ ID NO: 11] and conformational stability results from a disulfide bond involving the cysteine residues. Specific embodiments contemplated in this invention include peptides having the sequence RRETAWA [SEQ ID NO: 8] and CRRETAWAC [SEQ ID NO: 12]. Table 1 provides other peptides with this motif that bind to $\alpha_5\beta_1$. The fact that the cyclic peptide CRRETAWAC [SEQ ID NO: 12] binds to $\alpha_5\beta_1$ integrin shows that exocyclic amino acids are not necessary for binding. It is the core sequence that confers integrin binding ability on a peptide, and various exocyclic amino acids do not eliminate integrin-binding ability.

The identification of RRETAWA [SEQ ID NO: 8] as a motif that selectively binds to an integrin was surprising. The RRETAWA [SEQ ID NO: 7] motif bears no obvious similarity to the portion of the fibronectin sequence, or other ligand sequences, known to bind $\alpha_5\beta_1$ or other integrins. RRETAWA [SEQ ID NO: 8] binds to an integrin at the same site as RGD, or at a site that is in direct connection with the RGD-binding pocket in $\alpha_5\beta_1$ integrin, as shown in Example VI. Moreover, the binding of cells to immobilized RRETAWA [SEQ ID NO: 14] peptide is inhibited by EDTA, indicating that the interaction, like the binding of RGD to integrin, is divalent cation-dependent. The RRETAWA [SEQ ID NO: 8] peptide has two positive charges and one negative charge, which are likely to play a role in its binding to an integrin.

This invention also provides peptides binding to $\alpha_5\beta_1$ and containing the sequence RGDGX [SEQ ID NO: 2], in which X is an amino acid with a hydrophobic, aromatic side chain. In particular, this invention provides peptides having selectivity for $\alpha_5\beta_1$ integrin and containing the sequence RGDGX [SEQ ID NO: 2] in a constrained secondary conformation. Seven-membered cyclic peptides containing this sequence show relatively higher binding affinity than peptides of other cycle sizes. In particular, the invention contemplates peptides in which X is W or F. In one embodiment, the peptide contains the sequence CRGDGWC [SEQ ID NO: 13] or CRGDGFC [SEQ ID NO: 14] and the cyclic configuration results from a disulfide bond involving the cysteine residues. See Table 2.

This invention also provides peptides binding to $\alpha_v\beta_5$ and $\alpha_v\beta_3$ integrins and containing the sequence $X_1X_2X_3RGDX_4X_5X_6$ [SEQ ID NO: 3] in which the sequence is in a constrained secondary conformation conferred by two cyclizing bonds, wherein $X_1$, $X_3$, $X_4$ and $X_6$ are residues capable of forming a bridge and $X_2$ and $X_5$ are 1 to 5 amino acids. In one embodiment of the invention, the peptide contains the sequence $CX_2CRGDCX_5C$ [SEQ ID NO: 15]. Specific embodiments of this invention include peptides containing the sequence CDCRGDCFC [SEQ ID NO: 16], CDCRGDCLC [SEQ ID NO: 17] or CLCRGDCIC [SEQ ID NO: 18]. See Table 5. The double cyclic structure of these peptides is unusual. The presence of the two disulfide bonds was demonstrated by mass spectrometry.

This invention also provides peptides binding to $\alpha_v\beta_3$ integrin and containing the sequence RLD in a constrained secondary conformation. Nine-membered cyclic peptides containing this sequence show relatively higher binding affinity to $\alpha_v\beta_3$ compared to RLD-containing peptides of other cycle sizes. In one embodiment, the peptide contains the sequence $CX_1X_2RLDX_3X_4C$ [SEQ ID NO: 38]. The constrained configuration results from a disulfide bond involving the cysteine residues. Specific embodiments contemplated in this invention include peptides having the sequence CARRLDAPC [SEQ ID NO: 19] or CPSRLDSPC [SEQ ID NO: 20]. While the affinities of the RLD-containing peptides for $\alpha_v\beta_3$ are relatively low, these peptides have the useful feature that they are selective for the $\alpha_v\beta_3$ integrin compared to the $\alpha_v\beta_1$. See Example IX, and Table 3, infra.

As used herein, the term "peptide" refers to two or more amino acids joined by a peptide bond, which includes amino acid equivalents and other non-amino acid groups that retain the desired functional activity characteristic of a peptide of the present invention. Peptide equivalents can differ from conventional peptides by the replacement of one or more amino acid analogs with related organic acids (such as PABA), amino acids or the like or the substitution or modification of side chains or functional groups.

The peptides of this invention are synthetic. That is, they specifically exclude all naturally occurring peptides containing the described amino acid sequence motifs. This invention contemplates peptides in which the described motifs are included in longer peptides in which other amino acid sequences flank one or both ends of the motif. The peptides of this invention are not limited in size. However, the invention particularly contemplates peptides having fewer than about 50 amino acids in total. It also contemplates proteins in which the core motif sequence is artificially implanted within the sequence of the polypeptide, such as peptides manufactured by recombinant DNA technology or by chemical synthesis. The binding affinity of any peptide included herein can be tested by the affinity assays described herein and by other affinity assays known in the art.

As used herein, the term "amino acid" and any reference to a specific amino acid is generally meant to include naturally occurring proteogenic amino acids as well as non-naturally occurring amino acids such as amino acid analogs. In view of this broad definition, one skilled in the art would know that reference herein to an amino acid, unless specifically indicated otherwise, includes, for example, naturally occurring proteogenic (L)-amino acids, (D)-amino acids, chemically modified amino acids, including amino acid analogs such as penicillamine (3-mercapto-D-valine), naturally occurring non-proteogenic amino acids such as norleucine and chemically synthesized compounds that have properties known in the art to be characteristic of an amino acid.

The choice of including an (L)- or a (D)-amino acid in a peptide of the present invention depends, in part, on the desired characteristics of the peptide. For example, the incorporation of one or more (D)-amino acids can confer increased stability on the peptide in vitro or in vivo. The incorporation of one or more (D)-amino acids also can increase or decrease the binding activity of the peptide as determined, for example, using the binding assays described herein, or other methods well known in the art. In some cases, such as when treating a subject, it may be desirable to allow the peptide of the invention to remain active for only a short period of time. In those cases, the incorporation of one or more (L)-amino acids in the peptide can allow, for example, endogenous peptidases in the subject to digest the peptide in vivo, thereby limiting the subject's exposure to an active peptide.

As used herein, the term "amino acid equivalent" refers to compounds which depart from the structure of the naturally occurring amino acids, but which have substantially the structure of an amino acid, such that they can be substituted within a peptide which retains its biological activity. Thus, for example, amino acid equivalents can include amino acids as described above, which have side chain modifications or substitutions or which belong to a related class of organic acids such as amides or the like. The term "amino acid," as described above, is intended to include amino acid equivalents. The term "residues" also can refer to an amino acid or an amino acid equivalent and is synonymous with these terms. In general limited modifications can be made to a peptide without destroying its biological function.

As used herein, "binding" means specific, as opposed to non-specific, binding. Specific binding to an integrin can be determined by the ability of a peptide of this invention to compete with itself or with the peptide GRGDSP [SEQ ID NO: 21] for binding to the integrin. A distinctive characteristic of such binding is that the bound peptide can be detached or prevented from binding to an integrin by specific elution or initial contact, respectively, with the fibronectin-derived synthetic GRGDSP [SEQ ID NO: 21] peptide. See Pytela et al., *Cell,* 40:191–198 (1985) and Pytela et al., *Proc. Natl. Acad. Sci., USA,* 82:5766–5770 (1985), each of which is incorporated herein by reference. In addition, specific binding can be disrupted using an agent such as EDTA, which renders an integrin inactive, or using a denaturant such as low pH buffer, as described in the procedures set-out below.

As used herein a peptide "selectively binds" to an integrin if it binds with a 10-fold or higher affinity to that integrin as compared to another integrin as measured in the same type of binding assay. A peptide is "specific for" an integrin if it binds to that integrin with a 100-fold higher affinity as compared to another integrin as measured in the same type of binding assay. Alternatively, these values are derived from experiments in which the differences between the assay for the various integrins have been compensated for by comparison to a non-selective RGD peptide, GRGDSP [SEQ ID NO: 21].

As used herein the term "high binding affinity" refers to peptides that have an $IC_{50}$ of $1 \times 10^{-7}$ M or less in at least one competitive binding assay for an integrin. In the competitive binding assays described herein, the $IC_{50}$ value was determined by competition against a standard peptide of known binding affinity. Thus, CRRETAWAC [SEQ ID NO: 12] shows high binding affinity for $\alpha_5\beta_1$. See Examples VI and VII.

As used herein, "relative binding affinity" refers to the comparative affinity of two peptides for a particular integrin. Relative binding affinity can be determined by direct binding competition assays or by comparing binding affinity to a standard integrin-binding peptide, such as GRGDSP [SEQ ID NO: 21]. One measurement to determine relative binding affinity is the half-maximal inhibitory concentration ($IC_{50}$) of these peptides to inhibit binding of, for example, GRGDSP [SEQ ID NO: 21] to an integrin.

The peptides of the present invention can be synthesized using well known methods including methods of recombinant DNA technology and chemical synthesis. A linear peptide can be synthesized, for example, by the solid phase peptide synthesis method of Merrifield using an automated peptide synthesizer (*J. Am. Chem. Soc.,* 85:2149 (1964), which is incorporated herein by reference). Alternatively, a peptide of the present invention can be synthesized using standard solution methods well known in the art (see, for example, Bodanszky, M., *Principles of Peptide Synthesis* (Springer-Verlag, 1984), which is incorporated herein by reference). Such newly synthesized peptides can be obtained in relatively pure form using, for example, high performance liquid chromatography (HPLC) and can be characterized using, for example, mass spectrometry or amino acid sequence analysis. Although a purity of greater than 95 percent for the synthesized peptide is preferred, lower purity may be acceptable.

The peptides of this invention having the disclosed motif in a constrained secondary structure generally exhibit relatively higher binding affinity for integrins than peptides that do not have the motif in such a configuration and tend to exhibit more selectivity in integrin binding. As used herein, the terms "constrained secondary structure," "stabilized" and "conformationally stabilized" indicate that the peptide bonds comprising the peptide are not able to rotate freely in space but, instead, are maintained in a relatively fixed structure.

The importance of a constrained secondary conformation in the peptides of the invention is indicated by the fact that the binding activity of the cyclic peptide GACRRETAWACGA [SEQ ID NO: 6] was greatly decreased following reduction of the disulfide bond and alkylation of the cysteine residues.

Various methods for constraining the secondary structure of a peptide are well known in the art. In a particularly useful method, a newly synthesized linear peptide can be cyclized by the formation of a bond between reactive amino acid side chains. For example, a peptide containing a cysteine-pair can be synthesized and a disulfide bridge can be formed by oxidizing a dilute aqueous solution of the peptide with $K_3[F_e(CN)_6]$. The disulfide bridge can also be formed using penicillamine.

Other particularly useful ways for constraining the secondary structure of a newly synthesized linear peptide is to cyclize the peptide using any of various methods well known in the art. For example, a cyclized peptide of the present invention can be prepared by forming a peptide bond between non-adjacent amino acid residues as described, for example, by Schiller et al., *Int. J. Pept. Prot. Res.*, 25:171 (1985), which is incorporated herein by reference. Peptides can be synthesized on the Merrifield resin by assembling the linear peptide chain using $N^\alpha$-Fmoc-amino acids and Boc and tertiary-butyl protein, then, following release of the peptide from the resin, a peptide bond can be formed between the amino and carboxy termini.

Alternatively, a lactam such as an $\epsilon(\gamma$-glutamyl)-lysine bond can be formed between lysine and glutamic acid residues, a lysinonorleucine bond can be formed between lysine and leucine residues or a dityrosine bond can be formed between two tyrosine residues. Cyclic peptides can also be constructed to contain, for example, four lysine residues, which can form the heterocyclic structure of desmosine (see, for example, Devlin, *Textbook of Biochemistry*, 3d ed. (1992), which is incorporated herein by reference). Methods for forming these and other bonds are well known in the art and are based on well known rules of chemical reactivity.

A peptide of this invention also can be stabilized into a constrained secondary structure by incorporating the peptide into a larger peptide sequence that forms a known secondary structure. For example, a peptide of the present invention can be stabilized by incorporating it into a sequence that forms a helix such as an alpha ($\alpha$) helix or a triple helix, according to methods described, for example, by Dedhar et al., *J. Cell Biol.*, 104:585 (1987); by Rhodes et al., *Biochemistry*, 17:3442 (1978); and by Carbone et al., *J. Immunol.*, 138:1838 (1987), each of which is incorporated herein by reference.

As used herein the "members" of a cycle in a cyclized peptide are the amino acids in that cycle. Thus, for example, *CRRETAWAC* [SEQ ID NO: 12] is considered to be a nine-membered cycle. The "*" indicates the cysteine residue is involved in forming the disulfide bridge.

While certain cycle sizes may optimize the binding affinity and selectivity of a peptide for an integrin, this invention contemplates cycles of various sizes that contain the core sequence. Various cycle sizes can be obtained by varying the location of the bridge-forming elements within the peptide. Any person skilled in the art can determine whether the range of cycle sizes within which the peptide retains integrin-binding ability. Thus, for example, this invention contemplates the core sequence RLD contained within cycles of various sizes, themselves within longer peptides.

This invention contemplates many uses for the peptides described herein. They are useful in all the methods and materials for which other RGD peptides are useful. Insofar as they have high binding affinities, one need use less of the peptides of the invention than other RGD-containing peptides. Insofar as they bind integrins selectively or specifically, the peptides of this invention can be targeted more precisely than other RGD-containing peptides and, therefore, have a more specific effect and/or require less of a dose. Thus, the peptides of this invention represent an improvement over the known classes of RGD-containing peptides.

Bound to an affinity column or other appropriate purification system, the peptides of this invention are useful for isolating from a sample mixture the $\alpha_5$- and $\alpha_v$-containing integrins to which they bind. Therefore, this invention provides methods useful for isolating an integrin that binds to a peptide of this invention. The methods involve contacting the peptide with a sample mixture under ionic conditions to allow binding of an integrin to the peptide. The integrins are then separated from the peptides by methods well known in the art. Typically, the peptides are attached to an affinity column. The sample mixture is passed over the column under conditions that allow binding of the integrin to the peptide. Then the unbound molecules are removed by washing the column. The integrins are isolated by washing the column with a buffer that elutes the bound integrins from the peptides. An isolation method is described further in Example XIV.

The CRRETAWAC [SEQ ID NO: 12]-type peptides allow the specific isolation of the $\alpha_5\beta_1$ integrin. See Examples VI and VII.

The peptides of the present invention are particularly useful for these ends because they are readily and inexpensively synthesized and, therefore, are more readily available than, for example, the natural ligands of integrins or antibodies specific for an integrin or for an integrin subunit.

When bound to a solid surface, the peptides of this invention promote the attachment of cells bearing the appropriate integrin to that surface. A method useful for attaching cells to a substrate for cell culture involves binding a peptide of this invention to a substrate and contacting the substrate with the cell. The coating of the substrate with the peptide obviates the use of fibronectin in the medium, this providing better defined conditions for the culture as well as better reproducibility.

For example, Cytodex particles (Pharmacia, Piscataway, N.J.) are coated with gelatin. This makes it possible to grow the same number of adherent cells in a much smaller volume of medium than would be possible in dishes. The activity of these beads is generally dependent upon the use of fibronectin in the growth medium. Therefore the peptides of this invention are expected to produce an improved, chemically-defined coating for such purposes. Other surfaces or materials may be coated to enhance attachment, such as glass, plastic, agarose, synthetic resins or long-chain polysaccharides. (See, e.g., Glass et al., *Mat. Res. Soc. Symp Proc.*, 252:331–337 (1992) and Pierschbacher et al., U.S. Pat. No. 5,120,829.) The $\alpha_5\beta_1$-binding peptides provided in this invention allow the binding of cells containing the $\alpha_5\beta_1$ integrin. Moreover, the improved affinities of the peptides provided here allow the use of smaller amounts of the peptide for the coating, thus improving economies. This invention further provides devices comprising a peptide of this invention attached to the surface of a substrate. In one embodiment, the substrate is a cell culture dish.

The peptides of this invention are also useful as coatings on surfaces of implantable prosthetics, such as prosthetic blood vessels or vascular grafts where they attract and attach cells. Thus, this invention provides a device having a peptide of this invention attached to the surface of an implantable prosthetic. These implant devices generally are woven or knitted from nitrocellulose or polyester fiber, particularly Dacron (polyethylene terephthalate) fiber. Therefore, this invention provides methods useful for attracting cells to the surface of an implantable prosthetic involving attaching a peptide of this invention to the surface of the implantable prosthetic. A further method involves implanting the prosthetic into an individual. Thus, it is desirable to attract fibroblasts onto artificial tissue patches and endothelial cells onto vascular graphs.

The peptides of this invention are also useful in patch grafts or the like for aiding in wound healing. Accordingly, this invention provides patch grafts having a peptide of this invention that binds to $\alpha_5\beta_1$ integrin or the $\alpha_v$ integrin attached to a support matrix. The matrix can include a biodegradable molecule such as collagen, a glycosaminoglycan or a proteoglycan. Hyaluronic acid and chondroitin sulfate are two such materials. This invention further provides methods useful for promoting wound healing involving applying a patch graft of this invention to a wound.

RGD-containing adhesion peptides have been used in clinical trials in this manner. See, for example, Polarek et al., *Wounds: A Compendium of Clinical Research and Practice*, 6:46–53 (1994). The integrin-selectivities and affinities of the peptides of this invention also will provide advantages of cell type selectivity and economy in this method.

Many physiological events involve cell binding mediated through integrins. Thus, peptides that inhibit integrin-mediated binding are useful in therapies directed at regulating these events and, indeed, have been used for that purpose. For example, platelet binding to fibrinogen is mediated by the $\alpha_{IIb}\beta_3$ integrin. RGD-based anti-thrombotic compounds, which bind to this integrin and prevent the binding of platelets to fibrinogen, are currently in clinical trails. See, e.g., Tschopp et al., *Coronary Artery Disease*, 4:809–817 (1993).

Because the peptides of this invention bind to certain integrins they compete in vivo with RGD-containing molecules for binding to integrins. Administered to an individual, they are useful for preventing binding of integrin-bearing cells with their target molecules in vivo.

This invention provides methods useful for inhibiting the binding of integrin-bearing to RGD-containing molecules involving administering to an individual a peptide of this invention in an amount effective to inhibit the binding. In particular, this invention contemplates the use of high binding affinity peptides or peptides specific for one or more integrins in these methods.

Osteoporosis involves the attachment of bone-degrading osteoclasts to bone. Attachment of osteoclasts to bone is mediated by the $\alpha_v\beta_3$ integrin. See, e.g., Nesbitt et al., *J. Biol. Chem.*, 268:16737–45 (1993). Treatments are being developed for osteoporosis that depend on the ability of RGD peptides to prevent this attachment. Fisher et al., *Endocrinology*, 132:1411–1413 (1993). Accordingly, this invention provides methods useful for inhibiting the attachment of osteoclasts to bone involving administering to an individual a peptide of this invention that binds to $\alpha_v\beta_3$ integrin.

Angiogenesis, the formation of new blood vessels, involves the migration of endothelial cells which is dependent on the $\alpha_v\beta_3$ integrins. See, e.g., Brooks et al., *Science*, 264:569–571 (1994). Treatments for tumors based on the prevention of angiogenesis are being developed. Accordingly, this invention provides methods useful for inhibiting angiogenesis involving administering to an individual a peptide of this invention that bind to $\alpha_v\beta_3$ integrin.

RGD peptides inhibit tumor metastasis. (See, e.g., Humphries et al., *Cancer Biology*, 4:293–299 (1993)); Hardan et al., *Int. J. Cancer*, 55:1023–1028 (1993); Komazawa et al., *Carbohyd. Res.*, 21:299–307 (1993). Accordingly, this invention provides methods useful for inhibiting metastasis of tumors expressing integrins involving administering to an individual a peptide of this invention that bind to those integrins. In particular, the method is directed toward tumors expressing the $\alpha_5\beta_1$ and/or $\alpha_v\beta_3$ integrins.

Neointimal hyperplasia is characterized by smooth muscle cell migration from the media into the neointima. The disease has been inhibited by blocking $\alpha_v\beta_3$ integrin with an RGD peptide. See, e.g., Choi et al., *J. Vasc. Surg.*, pp 125–134 (January 1994). Accordingly, this invention provides methods useful for inhibiting migration of smooth muscle cells involving administering to an individual a peptide of the invention that binds to $\alpha_v\beta_3$ integrin.

As used herein, an individual is a vertebrate and, more particularly, a mammal, including a human.

The administration of the peptides in the methods of this invention must be in an amount effective for the binding of the peptide to cells bearing the target integrin. An effective amount of a peptide can be determined using the methods described herein. For example, as shown in FIG. 1, an effective amount of the claimed peptide can be determined using an assay to identify the concentration necessary to inhibit cell attachment.

In general, the peptides of this invention are administered to the individual in a pharmaceutically acceptable carrier. Pharmaceutically acceptable carriers are well known in the art and include aqueous solutions such as physiologically buffered saline or other solvents or vehicles such as glycols, glycerol, oils such as olive oil or injectable organic esters. A pharmaceutically acceptable carrier can contain physiologically acceptable compounds that act, for example, to stabilize the peptide of the present invention or increase the absorption of the peptide. Such physiologically acceptable compounds include, for example, carbohydrates, such as glucose, sucrose or dextrans, antioxidants, such as ascorbic acid or glutathione, chelating agents, low molecular weight proteins or other stabilizers or excipients. One skilled in the art would know that the choice of a pharmaceutically acceptable carrier, including a physiologically acceptable compound, depends, for example, on the route of administration of the integrin-binding peptide and on the particular physico-chemical characteristics of the specific peptide.

One skilled in the art would know that a pharmaceutical composition containing a peptide of the present invention can be administered to an individual by various routes, depending on the specific pathologic condition. For example, where the treatment is localized such as for inducing healing of a wound, a pharmaceutical composition comprising a peptide of the present invention coupled to a suitable carrier such as hyaluronic acid can be administered in the appropriate pharmaceutically acceptable formulation and administered topically. See, e.g., Polarek et al., *Wounds: A Compendium of Clinical Research and Practice*, 6:46–53 (1994). Alternatively, where treatment is systemic due, for example, to the presence in the subject of cancer, the composition can be administered parenterally, such as intravenously, intramuscularly, subcutaneously, intraorbitally, intracapsularly, intraperitoneally or intracisternally.

The total effective amount of a peptide of the present invention can be administered to a subject as a single dose, either as a bolus or by infusion over a relatively short period of time, or can be administered using a fractionated treatment protocol, in which the multiple doses are administered over a more prolonged period of time. One skilled in the art would know that the concentration of a peptide of the present invention required to obtain an effective dose in a subject depends on many factors including the age and general health of the subject as well as the route of administration and the number of treatments to be administered. In view of these factors, the skilled artisan would adjust the dose so as to provide an effective dose for a particular use.

The invention will now be described in greater detail by reference to the following examples. These examples are intended to illustrate but not limit the invention.

EXAMPLE I

Isolation of Vitronectin and Integrins

Vitronectin was purified from human plasma as described in Yatohgo et al., *Cell Struct. Funct.*, 13:281–292 (1988). Human plasma fibronectin was from the Finnish Red Cross. Peptides were synthesized on a Applied Biosystems Model 430A synthesizer (Foster City, Calif.) by standard Merrifield solid phase synthesis protocols and t-butoxycarbonyl chemistry. Peptides were cyclized after release from the resin by oxidizing with 0.01 M $K_3[Fe(CN)_6]$ in 1 mM $NH_4OAc$, pH 8, overnight at 25° C. After removing the excess of $H_2O$ by rotary evaporation, the peptides were lyophilized and finally purified by reverse-phase HPLC. A stock solution of the ACDCRGDCFCG [SEQ ID NO: 10] peptide was made in dimethyl sulfoxide at a concentration of 100 mM and was diluted in TBS or culture medium before use. Dimethyl sulfoxide alone was included as a control in all phage and cell attachment experiments. Other peptides used in this study were dissolved aqueous buffers at a concentration of 5 mM.

The $\alpha_v\beta_3$, $\alpha_v\beta_5$ and $\alpha_5\beta_1$ integrins were isolated from human placental extracts made in TBS buffer containing 0.1 M octyl glucoside, proteinase inhibitors and divalent cations (Pytela et al., *Methods Enzymol.*, 144:475–489 (1987). The $\alpha_v\beta_3$ and $\alpha_5\beta_1$ integrins were extracted into buffer containing 1 mM $MnCl_2$ and 1 mM $CaCl_2$ and isolated by affinity chromatography on Sepharose-coupled GRGDSPK peptide [SEQ ID NO: 22] (Pytela et al., *Methods Enzymol.*, 144:475–489 (1987)) and GAC*RRETAWAC*GA [SEQ ID NO: 6] peptide, respectively (Koivunen et al., *J. Cell. Biol.*, 124:373–380 (1994)). The $\alpha_v\beta_5$ integrin was isolated from extracts prepared with 1 mM $CaCl_2$ using affinity chromatography with vitronectin. The integrin bound by the GRGDSPK [SEQ ID NO: 22] peptide column was shown to be primarily $\alpha_v\beta_3$, because binding of labeled vitronectin to this integrin was blocked by the specific antibody LM609 (Cheresh and Spiro, *J. Biol. Chem.*, 262:17703–11 (1987)). In addition, most of the phage-binding activity in the $\alpha_v\beta_3$ preparation was captured into microliter wells coated with antibodies against the $\alpha_v$ or $\beta_3$ subunits as described previously (Koivunen et al., *J. Biol. Chem.*, 268:20205–10 (1993). The $\alpha_{IIb}\beta_3$ integrin was isolated from outdated platelets (Pytela et al., *Science*, 231:1559–1562 (1986)).

EXAMPLE II

Fibronectin Binding Assay

Polyclonal antibodies against the cytoplasmic tails of $\alpha_5$, $\alpha_v$ and $\beta_3$ subunits were prepared by immunizing rabbits with the synthetic peptides described according to the methods described by Freed et al., *EMBO J.*, 8:2955–2965 (1989); by Giancotti et al., *Cell*, 60:849–859 (1990); and by Vogel et al., *J. Cell. Biol.*, 121:461–468 (1993). The immunizing peptides were used to affinity purify the antibodies using methods well known in the art (Harlow et al., *Antibodies: A Laboratory Manual*, Cold Spring Harbor (1989), which is incorporated herein by reference).

The $\alpha_5\beta_1$ integrin was bound to $\alpha_5$ specific antibody-coated wells by incubating 300 $\mu$l of a placental extract per well in TBS buffer containing 0.1 M octylglucoside, 1 mM $CaCl_2$, 1 mM $MnCl_2$ and proteinase inhibitors overnight at 4° C., (Koivunen et al., *J. Biol. Chem.*, 268:20205–20210 (1993). Alternatively, the $\alpha_5\beta_1$ integrin was directly coated on plastic as described above. The wells were extensively washed with TBS containing 0.1% NP-40. $^{125}$I -labeled fibronectin (100,000 cpm per well) was incubated in the presence of competing peptides for 1 hour at 25° C. in 100 $\mu$l volume of TBS containing 0.1% NP-40 and 1 mM $MnCl_2$, as described by Koivunen et al., *J. Biol. Chem.* 268:20205–20210 (1993). After repeated washing, the bound radioactivity was quantitated with a gamma counter.

EXAMPLE III

Synthesis of Cyclic and Linear Peptides

The cyclic peptides GACRRETAWACGA [SEQ ID NO: 6] (*CRRETAWAC*) [SEQ ID NO: 12] and GA*CRGDC*LGA [SEQ ID NO: 5] (*CRGDC*) [SEQ ID NO: 37] were synthesized using an Applied Biosystems Model 430A synthesizer (Foster City, Calif.) and purified by reverse-phase HPLC. Aliquots of the cyclic peptides were linearized by reduction and alkylation. Briefly, 5 mg of peptide were incubated for 1 hour at 37° C. in 0.1 M Tris buffer (pH 8) containing 8 M urea and 100× molar excess of dithiothreitol. A 200× molar excess of iodoacetamide was added and the incubation was continued for 30 min in the dark. The peptide was dialyzed extensively against water using a membrane with 500 Da molecular weight cut off. The recovery of the peptide after dialysis was 43% as determined by UV absorbance.

EXAMPLE IV

Construction and Use of Phage Display Libraries

Peptide libraries were constructed in fuse 5 vector (Scott and Smith, *Science* 249:386–390 (1990)) as described previously (Koivunen et al., *J. Cell Biol.,* 124:373–380 (1994). The $CX_5C$, $CX_6C$, $CX_7C$ and $CX_9$ [SEQ ID NOS: 39–42] libraries were prepared using synthetic oligonucleotides containing core sequences $TGT(NNK)_5TGT$, $TGT(NNK)_6TGT$, $TGT(NNK)_7TGT$ and $TGT(NNK)_9$ [SEQ ID NOS: 43–46, respectively] (N=equal molar mixture of A, C, G, T; K=G or T), respectively. The oligonucleotides were made double-stranded by PCR amplification with 5 cycles, purified and ligated to the N-terminus of pIII gene of fuse 5 vector. The $CX_5C$, $CX_6C$, $CX_7C$ and $CX_9$ [SEQ ID NO: 39–42, respectively]. vectors were transfected into MC1061 cells using 16, 60, 263 and 250 electroporations, respectively. Bacteria were cultured for 24 hours in the presence of 20 µg/ml of tetracycline, and phage were collected from the supernatant by precipitation twice with polyethylene glycol. The phage pellets were dissolved at approximately $10^{13}$ transducing units (TU)/ml in TBS buffer containing 0.02% $NaN_3$ and stored at 4° C. The yields of the $CX_5C$, $CX_6C$, $CX_7C$ and $CX_9$ primary libraries were $3.5\times10^8$, $1.1\times10^9$, $4.5\times10^5$ and $3.5\times10^8$ clones, respectively.

A mixture of phage containing $7\times10^{10}$, $2.5\times10^{11}$, $2.5\times10^{11}$ and $4\times10^{11}$ TU from each of the $CX_5C$, $CX_6C$, $CX_7C$ and $CX_9$ [SEQ ID NOS: 39–42, respectively]. libraries, respectively, was screened with integrins coated on microliter wells essentially as described (Koivunen et al., *J. Biol. Chem.,* 268:20205–10 (1993)). In the first panning, the integrins were coated at 5 µg per well, and the library pool was incubated for 4 hours at 25° C. in TBS buffer containing 1% bovine serum albumin and 1 mM $MnCl_2$ ($\alpha_5\beta_1$, $\alpha_v\beta_3$), 1 mM $MgCl_2$ ($\alpha_{IIb}\beta_3$) or 1 mM $CaCl_2$ ($\alpha_v\beta_5$). Phage remained bound after extensive washing were eluted with a glycine buffer of pH 2.2. Any tight-binding phage possibly remaining bound to the wells were captured by incubating with concentrated K91kan bacteria (Smith et al., *Methods Enzymol.,* 217:228–257 (1993)) for 2 hours at 37° C. Bacteria were mixed with the low pH eluate and the phage were amplified. In the subsequent pannings, the integrins were coated at lower concentrations (100, 10 and 1 ng per well) to select high affinity phage sequences. Phage were sequenced from randomly selected clones as described (Koivunen et al., *J. Biol. Chem.,* 268:20205–10 (1993)).

Binding of individual cloned phage to integrins was studied in microliter wells as described in Koivunen et al., *J. Cell. Biol.,* 124:373–380 (1994). Phage binding to $\alpha_5\beta_1$ and $\alpha_v\beta_3$ were assayed in TBS buffer containing 1% BSA and 1 mM $MnCl_2$ and binding to $\alpha_v\beta_5$ in the presence of 1 mM $CaCl_2$. Phage that were bound were determined by their ability to infect F-pilus positive K91kan bacteria. Bacteria were grown overnight in microliter wells in the presence of tetracycline and the absorbance indicative of bacterial growth was read at 600 nm with an ELISA plate reader.

EXAMPLE V

Cell Attachment Assay

This example demonstrates the integrin-binding specificity of the peptides of the invention.

Cell lines expressing different integrins were used to examine peptide inhibition of integrin function. A human melanoma cell line, C8161, a fibroblast cell line, WI-38, and an osteosarcoma cell line, MG-63 (described by Seftor et al., *Canc. Res.,* 53:3411–3415 (1993); Vogel et al., *J. Biol. Chem.,* 265:5934–5937 (1990); and Pytela et al. (1985), supra, respectively, each of which is incorporated herein by reference) attach to fibronectin through $\alpha_5\beta_1$ integrin, as does B2/α27, a CHO cell line transfected with human $\alpha_5$. B2/C1, the control parental CHO line (Bauer et al., *J. Cell. Biol.* 116:477–487 (1992), which is incorporated herein by reference), attaches via $\alpha_v\beta_5$. CHO cells C11 and NIH 3T3 cells express the endogenous Chinese hamster and mouse $\alpha_5\beta_1$ integrins, respectively. The human melanoma cells, A375-M, attach to fibronectin through both $\alpha_5\beta_1$ and $\alpha_4\beta_1$ integrins (Mould et al., *J. Biol. Chem.* 265:4020–4024 (1990), which is incorporated herein by reference). CHO cell line B2/v7 express the $\alpha_v\beta_1$ integrin (Zhang et al., *J. Cell. Biol.* 122:235–242 (1993), which is incorporated herein by reference). The vitronectin-binding integrins $\alpha_v\beta_1$ and $\alpha_v\beta_3$ were assayed using the cell line HT-29 and IMR-90, respectively (Koivunen et al., *J. Biol. Chem.* 268:20205–20210 (1993)).

Cell lines expressing fibronectin-binding integrins were used to determine peptide activities against these integrins in the cell attachment assay described by Ruoslahti et al., *Meth. Enzymol.,* 144:803–831 (1982), which is incorporated herein by reference. Human plasma fibronectin was iodinated as described by Morla and Ruoslahti, *J. Cell Biol.,* 118:421–429 (1992), which is incorporated herein by reference. Vitronectin was obtained from Telios Pharmaceuticals (San Diego, Calif.). In different experiments, microliter wells were coated either with various concentrations of fibronectin or vitronectin or with a concentration that resulted in 50–70% maximum attachment for each cell type (B2/α27, 2 µg/ml; B2/v7, 4 µg/ml; HT29, 8 µg/ml; IMR90, 1 µg/ml). Peptide was coated on plastic by incubating at 37° C. for 2 hours in phosphate buffered saline containing 0.25% glutaraldehyde to crosslink the peptide. Free binding sites on the plastic were blocked using BSA. Approximately $1\times10^5$ cells per well were allowed to attach for 1 hour in the presence or absence of competing peptides. Bound cells were quantitated by staining with 0.1% amido black.

EXAMPLE VI

Determination of Relative Bindings Affinities of Peptides

Relative affinities of the CRRETAWAC [SEQ ID NO: 12] and CRGDC [SEQ ID NO: 37] peptides were determined by inhibition of binding of peptide-displaying phage to $\alpha_5\beta_1$ integrin. Peptide-displaying phage were constructed as described by Scott and Smith, *Science* 249:386–390 (1990) and Example IV. Microwell plates were coated with various integrins as described by Koivunen et al., *J. Biol. Chem.,* 268:20205–10 (1993) and Example II.

The binding of CRRETAWAC [SEQ ID NO: 12]-containing peptide ligands to $\alpha_5\beta_1$ integrin was performed as follows. RRETAWA [SEQ ID NO: 8]-displaying phage were incubated for 1 hour in the presence of various concentrations of the cyclic peptides containing CRRETAWAC [SEQ ID NO: 12] and containing CRGDC [SEQ ID NO: 37] in microliter wells coated with the $\alpha_5\beta_1$ integrin. Binding was quantitated by adding K91kan bacteria directly to the wells and growing the bacteria overnight at room temperature (Smith and Scott, *Meth. Enzymol.,* 217:228–257 (1993), which is incorporated herein by reference).

Figure 4:
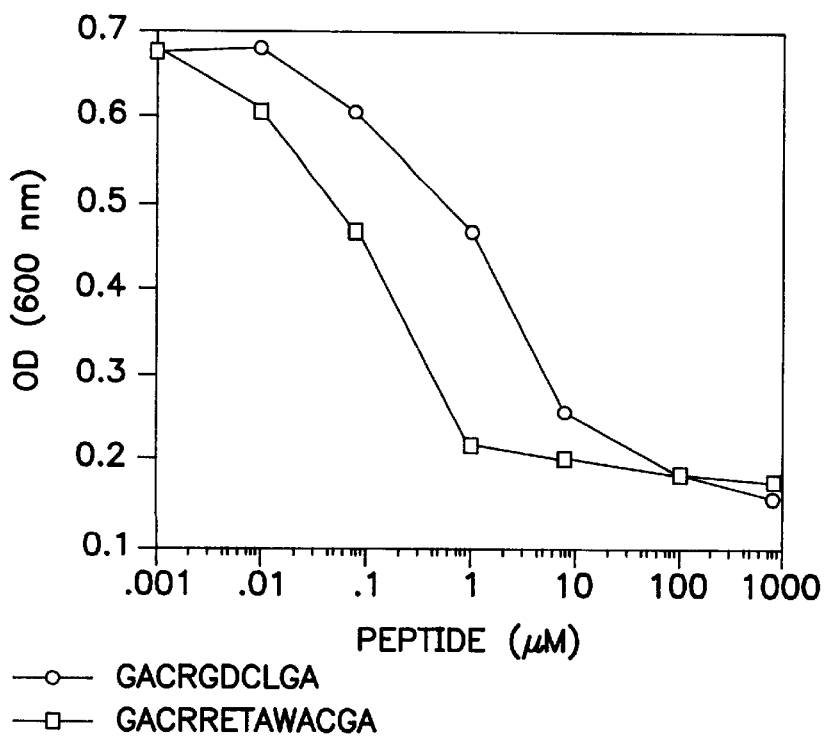
FIG. 4 shows the inhibition of binding of RRETAWA- [SEQ ID NO: 8] displaying phage to $\alpha_5\beta_1$ integrin by the cyclic peptides GACRRETAWACGA [SEQ ID NO: 6] and GACRGDCLGA [SEQ ID NO: 5].

FIG. 4 shows the inhibition of RRETAWA [SEQ ID NO: 8]-displaying phage binding to $\alpha_5\beta_3$ integrin by CRGDC [SEQ ID NO: 37] and CRRETAWAC [SEQ ID NO: 12]. The CRRETAWAC [SEQ ID NO: 12] motif inhibited at least 10 times more efficiently than the CRGDC [SEQ ID NO: 37] containing peptides. A control peptide GRGESP [SEQ ID NO: 23] had no effect.

Figure 2:
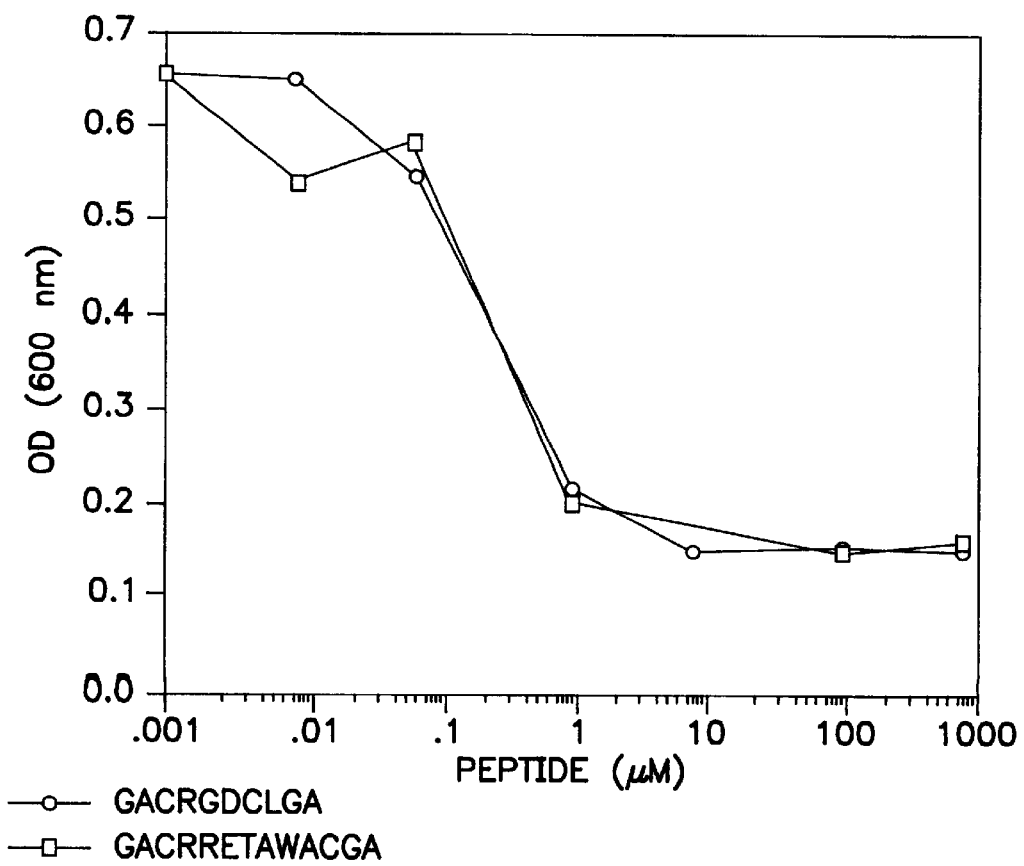
FIG. 2 shows the inhibition of binding of ELRGDGW [SEQ ID NO: 4]-displaying phage to $\alpha_5\beta_1$ integrin by synthetic cyclic peptides GACRGDCLGA [SEQ ID NO: 5] and GACRRETAWACGA [SEQ ID NO: 7].

Additional peptide motifs were tested as follows. ELRGDGW-displaying [SEQ ID NO: 4] phage were added together with various concentrations of the cyclic peptides containing CRRETAWAC [SEQ ID NO: 12] and containing CRGDC [SEQ ID NO: 37] into microliter wells coated with the $\alpha_5\beta_1$ integrin, incubated for 1 hour at room temperature and binding to wells was quantitated. As shown in FIG. 2, the CRRETAWAC [SEQ ID NO: 12] and CRGDC [SEQ ID NO: 9] inhibit the binding of ELRGDGW-displaying [SEQ ID NO: 4] phage to $\alpha_5\beta_1$ integrin to approximately the same degree.

Figure 3:
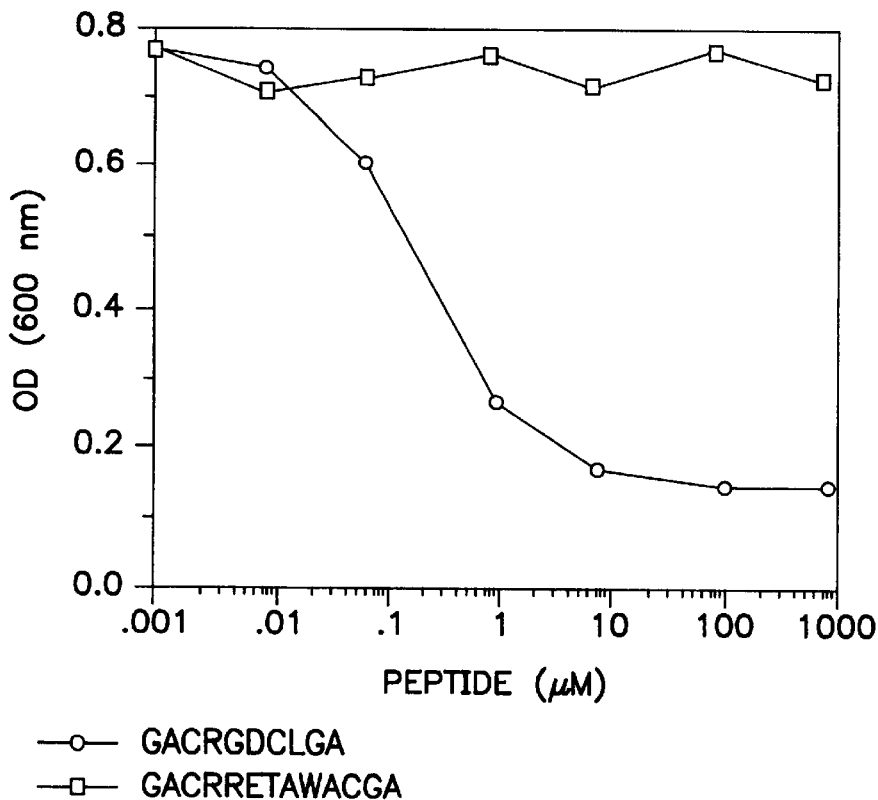
FIG. 3 shows the effect on binding of CRGDCL [SEQ ID NO: 7]-displaying phage to $\alpha_v\beta_3$ integrin by the cyclic peptides GACRRETAWACGA [SEQ ID NO: 6] and GACRGDCLGA [SEQ ID NO: 5].

The ability of CRRETAWAC [SEQ ID NO: 12] and CRGDC [SEQ ID NO: 37] containing peptides to inhibit binding of CRGDCL-displaying [SEQ ID NO: 7] phage to the microwells coated with $\alpha_v\beta_3$ integrin also was examined. CRGDCL-displaying [SEQ ID NO: 7] phage were added to a well and either cyclic GACRRETAWACGA [SEQ ID NO: 6] or cyclic GACRGDCLGA [SEQ ID NO: 5] was added to compete for binding. Binding was quantitated as described above. As shown in FIG. 3, the GACRRETAWACGA [SEQ ID NO: 6] peptide was ineffective in inhibiting binding of CRGDCL-displaying [SEQ ID NO: 7] phage to $\alpha_v\beta_3$ whereas the GACRGDCLGA [SEQ ID NO: 5] peptide completely inhibited the binding.

EXAMPLE VII

Specificity of RRETAWA for $\alpha_5\beta_1$ in Cell Attachment and Inhibiting Fibronectin Binding The results above indicated that the RRETAWA [SEQ ID NO: 8] motif exhibited high relative binding affinity and selectivity for $\alpha_5\beta_1$. To confirm this result, the RRETAWA [SEQ ID NO: 8]-containing peptide CRRETAWAC [SEQ ID NO: 12] was further tested in additional binding assays and in cell attachment assays. The methods used are identical to those described above.

Initially, CRRETAWAC [SEQ ID NO: 12] was examined for its ability to inhibit binding of fibronectin, which is the natural ligand for $\alpha_5\beta_1$. Briefly, $^{125}$I-fibronectin was incubated for 1 hour in the presence of competing peptides in microliter wells coated with $\alpha_5\beta_1$. Following incubation, the wells were washed and bound radioactivity was determined with a gamma counter. As shown in FIG. 1, the cyclic CRRETAWAC [SEQ ID NO: 12] peptide inhibits fibronectin binding equally as well as the cyclic CRGDC [SEQ ID NO: 37] peptide.

Figure 5:
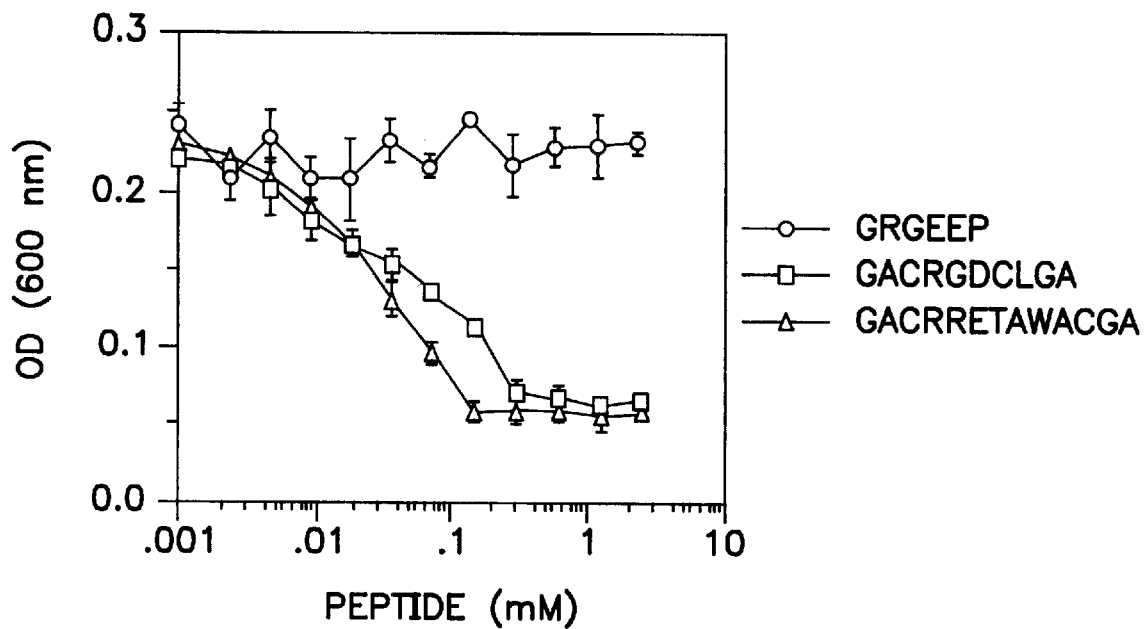
FIG. 5 shows the inhibition of $\alpha_5\beta_1$-mediated cell attachment to fibronectin by synthetic peptides.
Figure 6:
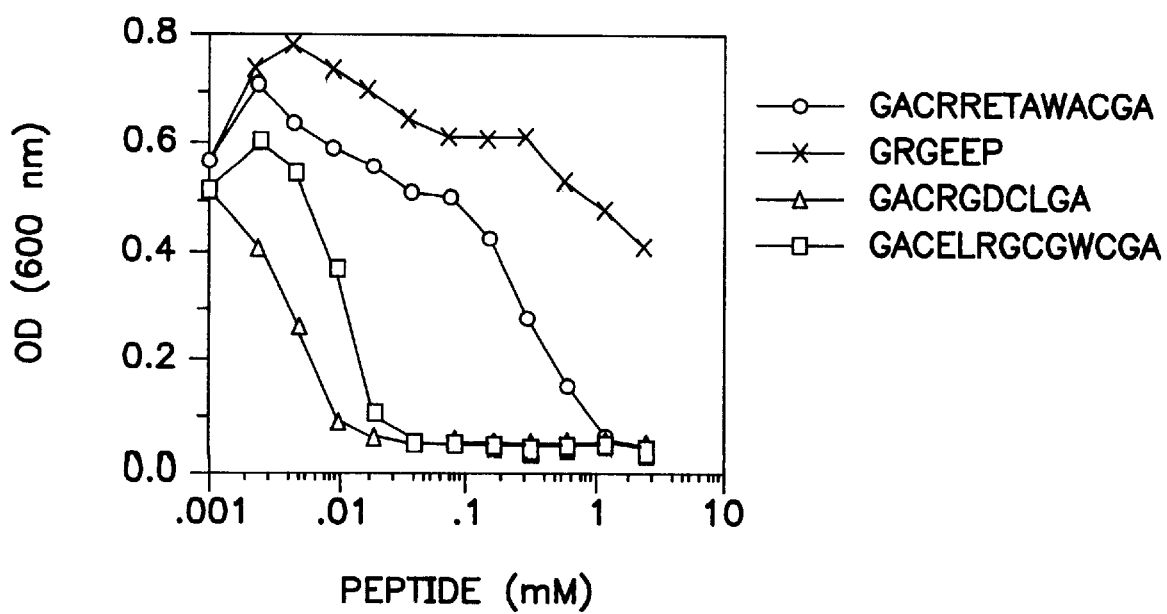
FIG. 6 shows the inhibition of $\alpha_v\beta_1$-mediated cell attachment to fibronectin by synthetic peptides.
Figure 7:
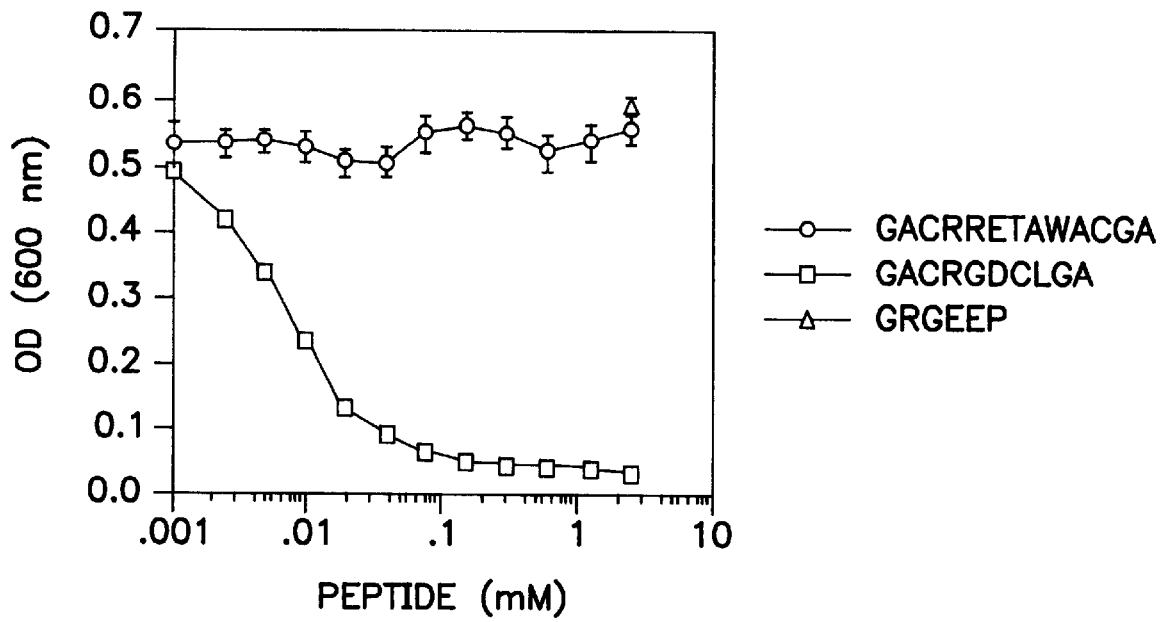
FIG. 7 shows the inhibition of $\alpha_v\beta_5$-mediated cell attachment to vitronectin by synthetic peptides.

Inhibition of cell attachment mediated by either fibronectin- or vitronectin-binding integrins was performed to determine peptide specificity in a biologically relevant system. The assays and cell lines were performed as described above. FIGS. 5 and 6 show the results of cell attachment mediated by the fibronectin binding integrins $\alpha_5\beta_1$ and $\alpha_v\beta_1$. FIG. 7 shows cell attachment mediated by the $\alpha_v\beta_5$ vitronectin binding integrin.

The cell attachment inhibition assays confirm that the RRETAWA [SEQ ID NO: 8] peptide is more efficient at inhibiting binding to $\alpha_5\beta_1$ than the cyclic CRGDCL [SEQ ID NO: 7] peptide (FIG. 5). The IC$_{50}$ of CRRETAWAC [SEQ ID NO: 12]-inhibited $\alpha_5\beta_1$-mediated cell attachment to fibronectin was $3\times10^{-5}$ M. The peptide also inhibited cell attachment to a 110 kDa fragment of fibronectin that contains the cell attachment domain. Reduction and alkylation of the disulfide bond reduced the activity of the peptide about 50x. The control peptide GRGESP [SEQ ID NO: 23] had no effect on binding (FIG. 5).

The results in FIG. 5 were obtained using B2/α27 cells, which express the human $\alpha_5$ subunit expressed from a transfected cDNA. However, similar results were obtained using the C8161, MG-63 and WI-38 human cell lines, which all express $\alpha_5\beta_1$ The attachment of A375-M cells was only partially inhibited by CRRETAWAC [SEQ ID NO: 12], possibly because this cell line expresses other fibronectin-binding integrins such as $\alpha_4\beta_1$ (Mould et al. (1990), supra). However, CRRETAWAC [SEQ ID NO: 12] could not block attachment of CHO C11 cells or mouse NIH 3T3 cells to fibronectin, indicating the peptide may be species-specific.

When tested against another fibronectin binding integrin, $\alpha_v\beta_1$s. however, the RRETAWA [SEQ ID NO: 8] peptide was greater than 100x less active than the cyclic RGD peptide and about 40x less active than another integrin binding peptide studied, CELRGDGWC [SEQ ID NO: 24] (FIG. 6). Finally, when tested against $\alpha_v\beta_5$ cell attachment to vitronectin, the RRETAWA [SEQ ID NO: 8] containing peptide was essentially devoid of activity at all concentrations tested (FIG. 7). Combined with the binding data discussed above, these results demonstrate that the GACR-RETAWACGA [SEQ ID NO: 6] peptide exhibits high activity and selectivity for the $\alpha_5\beta_1$ integrin.

In addition to the inhibition of cell attachment to natural ligands, attachment and inhibition assays were performed using the GACRRETAWACGA [SEQ ID NO: ] peptide as substrate. The microliter well were coated with GACRRE-TAWACGA [SEQ ID NO: 6] using glutaraldehyde as described above. Briefly, peptide was coated on plastic by incubating at 37° C. for 2 hours in phosphate buffered saline containing 0.25% glutaraldehyde to crosslink the peptide and free binding sites on the plastic were blocked using BSA. The wells were then saturated with BSA followed by the addition of 50,000 B2/α27 or B2/Cl cells in the presence or absence of the indicated inhibitor. The B2/α27 cells express $\alpha_5\beta_1$ whereas the B2/Cl do not. Bound cells were quantitated by staining with 0.1% amido black.

Figure 8:
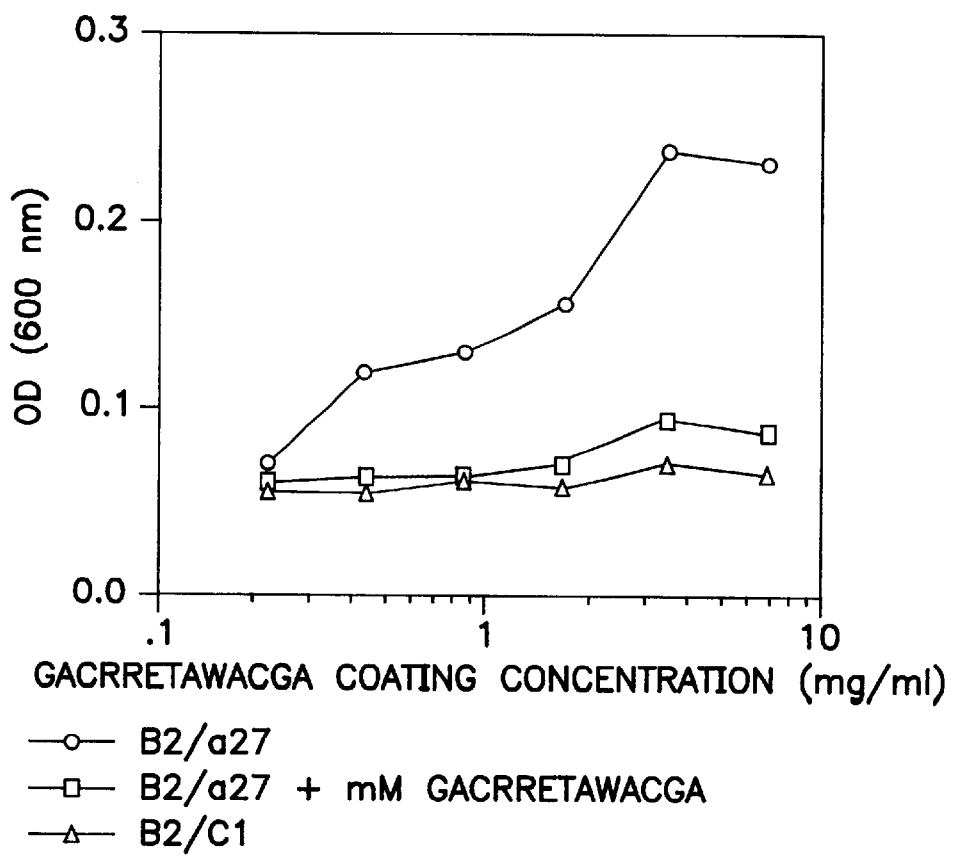
FIG. 8 shows the binding of $\alpha_5\beta_1$-expressing cells and $\alpha_v\beta_5$-expressing cells to the GACRRETAWACGA [SEQ ID NO: 6] peptide.

As shown in FIG. 8, the RRETAWA [SEQ ID NO: 8]-containing peptide promoted $\alpha_5\beta_1$-mediated adhesion (compare the B2/α27 attachment with the B2/C1). This attachment was inhibited by the RRETAWA-[SEQ ID NO: 8] containing peptide (1 mM) as well as by CRGDC [SEQ ID NO: 8] (1 mM) and by EDTA (10 mM). The $\alpha_v\beta_1$-expressing B2/v7 cells also bound to the peptide, however, a peptide coating concentration of 1 mg/ml was required to produce significant attachment. Cell lines that do not express these integrins or express a non-human $\alpha_5\beta_1$ integrin did not attach to immobilized CRRETAWAC [SEQ ID NO: 12].

EXAMPLE VIII

CRX$_1$ETX$_2$WX$_3$C Peptides Recognized by the $\alpha_5\beta_1$ Integrin

The peptides CRRETAWAC [SEQ ID NO: 12] and CRSETYWKC [SEQ ID NO: 25] were both found to selectively bind the $\alpha_5\beta_1$ integrin. Therefore, a library of peptides having the motif common to both, X$_4$CRX$_1$ETX$_2$WX$_3$C [SEQ ID NO: 26] was created in a manner similar to the other libraries described herein and tested for binding to the $\alpha_5\beta_1$ integrin. Second and third pannings allowed identification of many peptides selective for the $\alpha_5\beta_1$ integrin. See Table 1. A large number of these contained the motif CRRETAWAC [SEQ ID NO: 12], indicating that the motif retains binding ability even with the incorporation of a variety of different amino acids in exocyclic positions.

EXAMPLE IX

RGD and Related Peptides Recognized by the $\alpha_5\beta_1$ Integrin

A pool of the libraries expressing peptides of different length was first screened with the $\alpha_5\beta_1$ integrin. Total of 40 different sequences were obtained, of which 2, 20 and 18 were derived from the $CX_5C$, $CX_6C$ and $CX_9$ [SEQ ID NOS: 39,40 and 42, respectively]. libraries, respectively (Table 2). Increasing the stringency of the panning enriched a glycine residue at the position C-terminal to the RGD sequence, as has been found earlier (Koivunen et al., *J. Biol. Chem.*, 268:20205–10 (1993); Koivunen et al., *J. Cell Biol.*, 124:373–380 (1994)). The next residue C-terminal to glycine was tryptophan, phenylalanine or another hydrophobic amino acid. The third position C-terminal to RGD was also frequently occupied by a large hydrophobic amino acid. The most often occurring sequence was the $CX_6C$ peptide CRGDGWMC [SEQ ID NO: 27], which was found 10 times. The $CX_5C$ sequence CRGDGWC [SEQ ID NO: 13] was found 8 times.

All the sequences derived from the $CX_9$ library contained another cysteine in the $X_9$ [SEQ ID NO: 42] portion. In the RGD-containing peptides, the location of the second cysteine varied and included $CX_3CX_4$, $CX_5CX_3$, $CX_6CX_2$ $CX_7CX$ and $CX_8C$. The $CX_3CX_4$ sequence contained the CRGDCL [SEQ ID NO: 7] sequence we isolated earlier using a linear $X_6$ library (Koivunen et al., *J. Biol. Chem.*, 268:20205–10 (1993)).

The $\alpha_5\beta_1$-binding motif NGR (Koivunen et al., *J. Biol. Chem.*, 268:20205–10 (1993); Koivunen et al., *J. Cell Biol.*, 124:373–380 (1994)) was found in two clones. The peptides had a structure $CX_8C$ and had similarities to the NGRAHA [SEQ ID NO: 28] sequence originally isolated from the $X_6$ library (Koivunen et al., *J. Biol. Chem.*, 268:20205–10 (1993)). Eight $CX_8C$ sequences derived from the $CX_9$ library lacked the RGD or NRG motifs and were not studied further.

EXAMPLE X

Sequences Selected by the $\beta_3$ Integrins

A majority (42 out of 50) of the phage sequences selected by the $\alpha_v\beta_3$ integrin contained the RGD sequence (Table 3). Most of them were from the $CX_7C$ library. Two sequences were derived from the $CX_9$ library and had a structure $CX_8C$. In contrast to the $\alpha_5\beta_1$-binding sequences, the most common residue C-terminal to the RGD sequence was serine, but this position was also occupied by many other residues such as threonine, alanine or a basic amino acid. The next residue towards the C-terminus was usually a large hydrophobic amino acid such as phenylalanine, but several other amino acids were also found at this position, even after high affinity selection.

Four clones displayed apparent RGD homologs, in which the small glycine residue was substituted by leucine (3 clones) or serine (1 clone). This includes the peptides CARRLDAPC [SEQ ID NO: 19] and CPSRLDSPC [SEQ ID NO: 20]. Finally, four phage sequences were isolated that did not contain the RGD motif. The sequences were hydrophobic and did not show clear homology to any sequence in vitronectin (Suzuki et al., *EMBO J.* 4:2519–2524 (1985)).

Panning with the $\alpha_{IIb}\beta_3$ integrin yielded sequences somewhat similar to those selected by $\alpha_v\beta_3$. The sequences could be categorized into two groups, those containing the RGD motif and those containing variations, where the glycine or arginine residue of RGD was replaced (Table 4). The glycine was substituted by quite different amino acids such as serine, threonine, leucine, alanine, glutamine, histidine and methionine, and some sequences lacked the glycine displaying only RD. The KGD homolog was found in one phage clone among the 35 sequences obtained.

The RGD-containing sequences favored by $\alpha_{IIb}\beta_3$ differed from those selected by $\alpha_5\beta_1$ and $\alpha_v\beta_3$ in that aromatic residues Trp, Phe, or Tyr were enriched at a position immediately C-terminal to the RGD sequence. In addition, several sequences contained one or two basic residues outside the RGD.

EXAMPLE XI

Sequences Selected by the $\alpha_v\beta_5$ Integrin

Most of the RGD-containing sequences bound to the $\alpha_v\beta_5$ integrin originated from the $CX_7C$ and $CX_9$ libraries (Table 5). Furthermore, all the 18 $CX_9$ peptides obtained had a structure $CX_8C$. The peptide binding of $\alpha_v\beta_5$ was similar to that of $\alpha_v\beta_3$ in that the residue C-terminal to RGD often was serine or threonine and the following position was phenylalanine. The RGDSF [SEQ ID NO: 31] or RGDTF [SEQ ID NO: 32] sequences occurred in 13 of 39 RGD sequences determined. There was no enrichment of a particular amino acid in the positions N-terminal to the RGD sequence. The sequences selected by the other three integrins also showed no predominance for any particular amino acid at those positions.

A search for high affinity sequences yielded four sequences with the CRGDC [SEQ ID NO: 37] motif, each from the $CX_7C$ library. These sequences contained two additional cysteines, suggesting the presence of two disulfide bonds. Three of these sequences had the structure CXCRGDCXC [SEQ ID NO: 15] and one CRGDCCXXC [SEQ ID NO: 33].

The $\alpha_v\beta_5$ integrin also selected non-RGD sequences, all from the $CX_9$ library that had two or three basic residues and often contained also a glutamine residue. Five of these sequences had a structure $CX_8C$ and one $CX_7CX$, but another five lacked the second cysteine. These sequences were found only after the second, but not subsequent, pannings and the phage bound weakly to the integrin.

EXAMPLE XII

Studies with Synthetic Peptides in Phage Binding Assay

Figure 9:
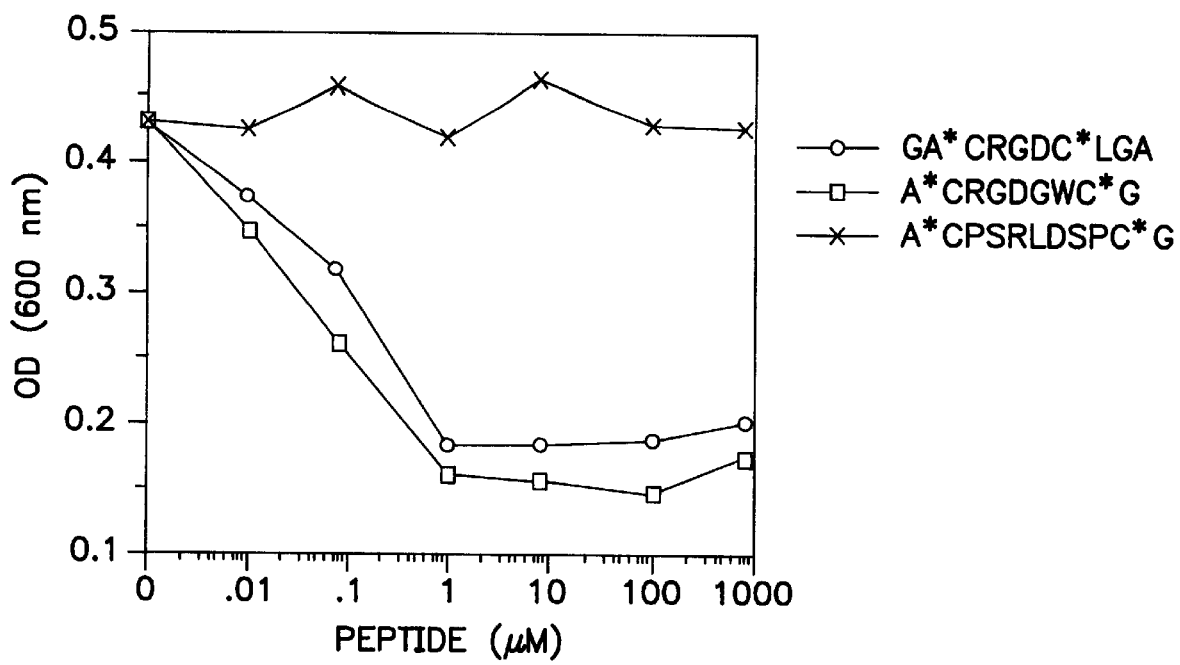
FIG. 9 shows inhibition of phage attachment to the $\alpha_5\beta_1$ integrin by cyclic RGD-containing peptides. Phage clone containing the RGDGW [SEQ ID NO: 9] sequence was incubated for 1 hour in integrin-coated microliter wells in the presence of the competing peptides. After extensive washing, the phage remained bound were determined as described in Example XII. The results show means from duplicate wells.

To test whether the RGDGW [SEQ ID NO: 9] sequence has a high affinity for $\alpha_5\beta_1$ as suggested by the phage, we synthesized the cyclic peptide A*CRGDGWC*G [SEQ ID NO: 34]. This peptide, derived from the $CX_5C$ library was chosen because the phage expressing the peptide was among the best binders of the integrin and consistently showed higher avidity than phage expressing the previously identified active binding sequences RRETAWA [SEQ ID NO: 8] and CRGDCL [SEQ ID NO: 7]. The A*CRGDGWC*G [SEQ ID NO: 34] peptide was 5-fold more active in inhibiting the binding of RGD-displaying phage to $\alpha_5\beta_1$ than the *CRGDC* [SEQ ID NO: 37] peptide (FIG. 9). We also synthesized a peptide according to one of the RLD-containing phage. One of the RGD homologs found in this study, the peptide A*CPSRLDSPC*G [SEQ ID NO: 35] that was selected by the $\alpha_v\beta_3$ integrin from the $CX_7C$ library, bound to $\alpha_v\beta_3$ but not to $\alpha_5\beta_1$. Consistent with this, the synthetic peptide A*CPSRLDSPC*G [SEQ ID NO: 35] showed no inhibition of RGD phage binding to $\alpha_5\beta_1$ (FIG. 9).

The ACDCRGDCFCG peptide [SEQ ID NO: 10] was one of the apparent double sulfide-bonded peptides that were bound strongly to the $\alpha_v\beta_5$ integrin. Phage attachment experiments indicated that the phage expressing this peptide bound preferentially to the $\alpha_v\beta\beta_5$ integrin. Since we do not know which cysteines may pair with each other in phage, no attempt was made to control the formation of disulfide bonds in the synthetic peptide. Oxidation after release of the peptide from the synthesis resin yielded one major peak in that eluted significantly earlier than the non-oxidized peptide run separately. This suggests homogenous disulfide bonding of the peptide. One disulfide bond is possibly formed between the cysteines flanking the RGD sequence, as the *CRGDC* [SEQ ID NO: 37] peptide is active. A second disulfide bridge would then form between the $CX_7C$ cysteines, although we cannot exclude the possibility of a mixture of different bonds. Mass spectrometry confirmed that the peptide do contain two disulfide bonds.

Figure 10:
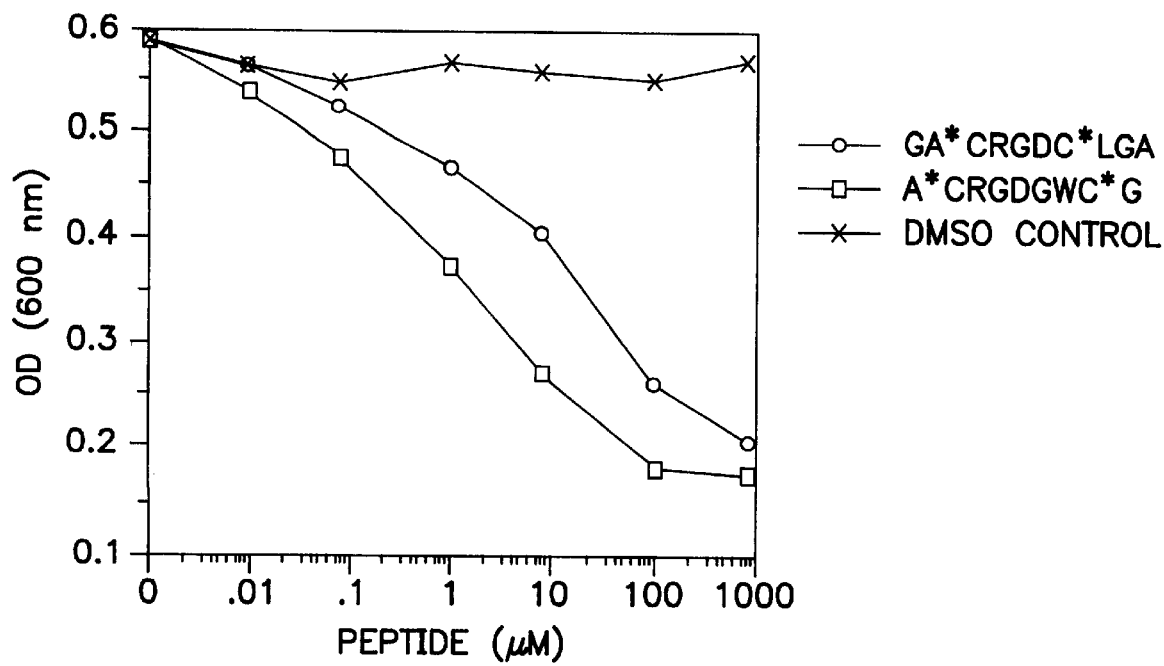
FIG. 10 shows inhibition of phage binding to the $\alpha_v\beta_5$ integrin by cyclic RGD peptides. Phage containing the ACDCRGDCFCG [SEQ ID NO: 10] sequence were incubated for 1 hour in integrin-coated wells in the presence of the competing peptides or dimethyl sulfoxide solvent as a control. The bound phage were determined as described herein. The results show means from duplicate wells.

The cyclized ACDCRGDCFCG [SEQ ID NO: 10] peptide was 10-fold more potent than the single disulfide bond-containing peptide *CRGDC* [SEQ ID NO: 37] in inhibiting the binding of RGD-containing phage to $\alpha_v\beta_5$ (FIG. 10). Phage binding to $\alpha_v\beta_3$ was inhibited by the ACDCRGDCFCG [SEQ ID NO: 10] peptide 5-fold better than by *CRGDC* [SEQ ID NO: 37], indicating that the ACDCRGDCFCG [SEQ ID NO: 10] peptide binds to both of these $\alpha_v$ integrins. Dimethyl sulfoxide solvent was included as a control and had no effect on phage binding at concentrations up to 1%.

Further phage binding experiments showed that the RLD-containing peptide A*CPSRLDSPC*G [SEQ ID NO: 35] had partial selectivity towards the $\alpha_v\beta_3$ integrin but that its affinity was low. In $\alpha_v\beta_3$ and $\alpha_v\beta_5$ binding assays, the peptide had a 100-fold and 1000-fold lower activity than *CRGDC* [SEQ ID NO: 37], respectively. The low affinity may partially be due to the tendency of the peptide precipitate at neutral pH.

EXAMPLE XIII

Inhibition of Cell Attachment with Synthetic Peptides

Figure 11:
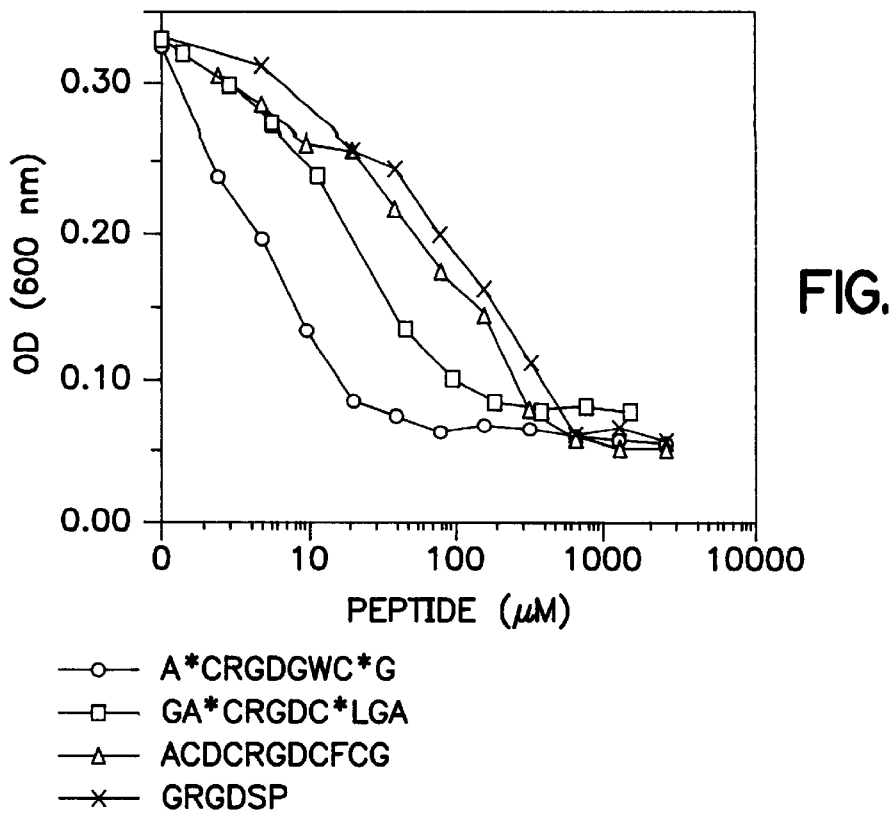
FIGS. 11 to 13 show peptide inhibition of cell adhesion. The effect of the synthetic peptides were tested as follows.

Cell attachment experiments confirmed the high affinities of the RGDGW- [SEQ ID NO: 9] and double disulfide bond-containing peptides inferred from the phage assays. The A*CRGDGWC*G [SEQ ID NO: 34] peptide was a potent inhibitor of $\alpha_5\beta_1$-mediated cell attachment to fibronectin. A*CRGDGWC*G [SEQ ID NO: 34] inhibited the attachment of B2/α27 cells, which attach to fibronectin via the $\alpha_{5\beta_1}$ integrin composed of human $\alpha_5$ and CHO $\beta_1$, with a $IC_{50}$ of 6 $\mu$M; it was 7-fold more potent than the *CRGDC* [SEQ ID NO: 37] (FIG. 11) or *CRRETAWAC* [SEQ ID NO: 12] peptides. Similar results were obtained with MG 63 cells, where A*CRGDGWC*G [SEQ ID NO: 34] inhibited at $IC_{50}$ of 10 $\mu$M and was 4-fold more potent than *CRRETAWAC* [SEQ ID NO: 12]. As compared to the standard linear peptide GRGDSP [SEQ ID NO: 21], A*CRGDGWC*G [SEQ ID NO: 34] showed about 50-fold improvement in activity. Notably, the double disulfide bond-containing ACDCRGDCFCG [SEQ ID NO: 10] peptide had a significantly decreased activity toward $\alpha_5\beta_1$ as compared to the smaller *CRGDC* [SEQ ID NO: 37] peptide and was only slightly better than the linear GRGDSP [SEQ ID NO: 21] peptide. We also prepared another synthetic RGDGW-containing [SEQ ID NO: 9] peptide, GAC*ELRGDGWC*GA[SEQ ID NO: 36] that was derived from the $CX_7C$ [SEQ ID NO: 41] library (Koivunen et al., J. Cell Biol., 124:373–380 (1994)). This $CX_7C$ peptide was 10-fold less active than the shorter $CX_5C$ [SEQ ID NO: 39] peptide.

Figure 12:
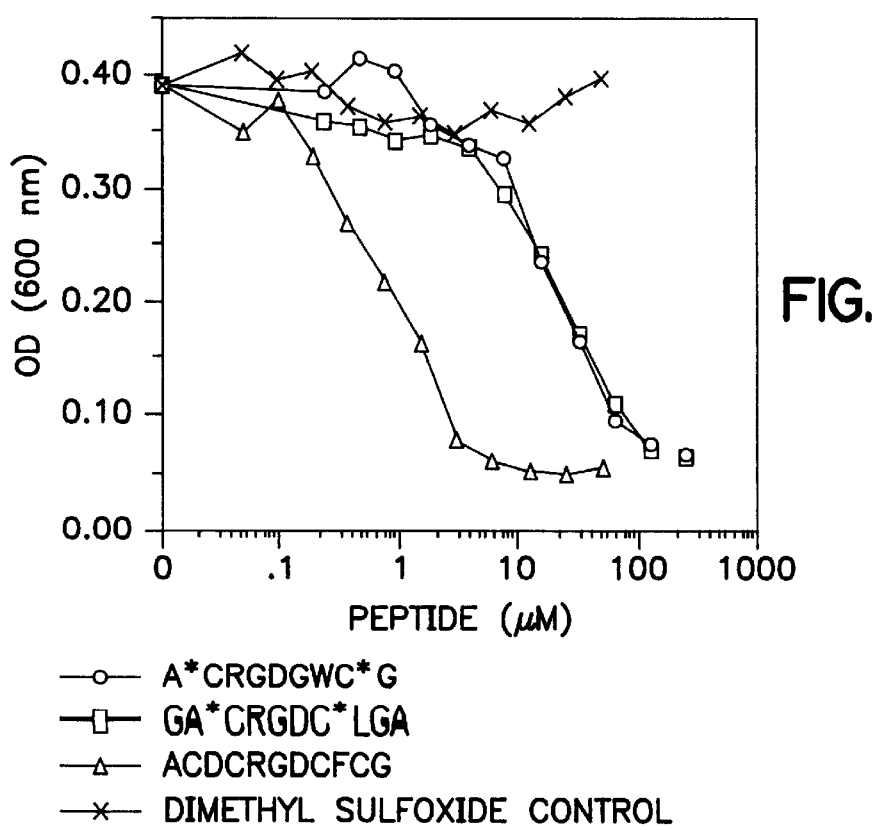

The ACDCRGDCFCG [SEQ ID NO: 10] peptide was a highly potent inhibitor of $\alpha_v\beta_5$-mediated cell attachment to vitronectin (FIG. 12). With HT-29 cells, the peptide inhibited at $IC_{50}$ of 0.6 $\mu$M and had a 40-fold higher affinity than the single disulfide bond-containing peptides *CRGDC* [SEQ ID NO: 37] and A*CRGDGWC*G [SEQ ID NO: 34]. Similar results were obtained with UCLA-P3 cells, where ACDCRGDCFCG [SEQ ID NO: 10] ($IC_{50}$=0.6 $\mu$M) showed a 20-fold enhancement in activity relative to *CRGDC* [SEQ ID NO: 37]. Dimethyl sulfoxide at the concentrations corresponding to those added with the peptide had no effect on cell adhesion.

Figure 13:
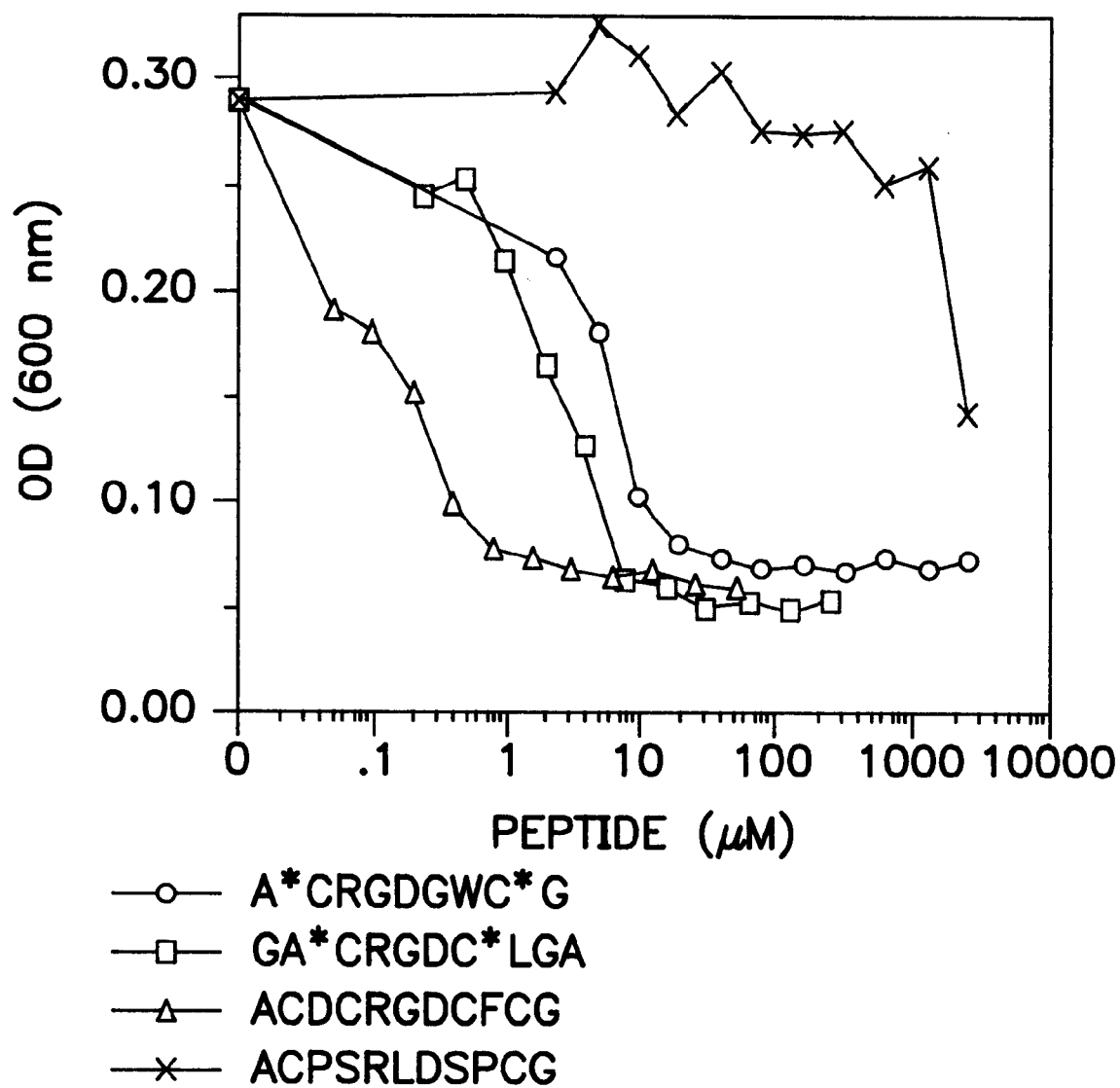

The ACDCRGDCFCG [SEQ ID NO: 10] peptide also had a higher affinity for the $\alpha_v\beta_3$ integrin than the single-disulfide bond-containing peptides. At $IC_{50}$ of 0.2 $\mu$M, the peptide was a 20-fold more effective inhibitor of attachment of IMR-90 cells to vitronectin than *CRGDC* [SEQ ID NO: 37] (FIG. 13). The RLD-containing cyclic peptide A*CPSRLDSPC*G [SEQ ID NO: 35] showed inhibitory activity only at concentrations higher than 1 mM.

EXAMPLE XIV

Isolation of the $\alpha_5\beta_1$ Integrin by Peptide Affinity Chromatography

Adhesive peptides are useful tools for receptor purification. For instance, the linear peptide GRGDSPK [SEQ ID NO: 22] coupled to Sepharose may be used for affinity purification of $\alpha_v\beta_3$ or the platelet receptor $\alpha_{IIb}\beta_3$ (Pytela et al., Methods Enzymol., 144:475–489 (1987)). Although the peptide sequence derives from fibronectin, the fibronectin receptor $\alpha_5\beta_1$ integrin does not bind this column presumably because the affinity of this interaction is too low without additional receptor contacts which occur in the natural ligand. This was the first demonstration that differential affinity for a peptide could be used to selectively isolate an integrin.

The cyclic peptide GA*CRRETAWAC*GA[SEQ ID NO: 6] binds specifically to $\alpha_5\beta_1$ with high affinity. An application for this peptide in the purification of $\alpha_5\beta_1$ from human placental tissue by a method based upon the procedure for purification of the vitronectin receptor by affinity for the peptide GRGDSPK [SEQ ID NO: 22] is described here. Indeed, GRGDSPK [SEQ ID NO: 22] and the GA*CRRETAWAC*GA peptide [SEQ ID NO: 6] columns may be run in tandem to simultaneously purify both $\alpha_5\beta_1$ and $\alpha_v\beta_3$ from the same starting material.

The $\alpha_5\beta_1$ affinity resin is prepared by coupling 75 mg of peptide GA*CRRETAWAC*GA[SEQ ID NO: 6] to 5 ml of cyanogen bromide-activated 4B Sepharose according to manufacturer's instructions (Pharmacia, Uppsala, Sweden). The peptide resin is packed into a 1 cm diameter column and equilibrated [in TBS (tris buffered saline) with 1 mM $CaCl_2$, 1 mM $MnCl_2$, and 100 mM octyl-β-D-glucopyranoside (Calbiochem, La Jolla, Calif.)]. The tissue is washed three times by addition of 400 ml of ice cold TBS containing proteinase inhibitors (1 mM PMSF, 0.5 $\mu$g/ml leupeptin, 0.5 $\mu$/ml pepstatin) and 10 minutes centrifugation at 10,000 rpm. The washed tissue is mixed with a minimal volume (200 ml) of ice-cold extraction buffer [TBS containing 1 mM $CaCl_2$, 1 mM $MnCl_2$, 100 mM octyl-β-D-glucopyranoside and proteinase inhibitors] and incubated for 4 hours. After centrifugation for 20 minutes at 10,000 g, the supernatants are pooled and passed over the peptide column that has previously been equilibrated in TBS containing 1 mM $CaCl_2$, 1 mM $MnCl_2$, and 100 mM octyl-β-D-glucopyranoside. The column is then washed with 200 ml of wash buffer [TBS containing 1 mM CaCl$_2$, 25 mM octyl-β-D-glucopyranoside and proteinase inhibitors]. For most purposes, further purification is not required. After dialysis in TBS containing 1 mM MnCl$_2$ and 0.02% NaN$_3$, the integrin can be stored at 4° C. for at least one month or aliquots may be quickly frozen with liquid nitrogen and stored at 80° C. Final yield of 100 μg obtained by this method is comparable to other methods of purification (Pytela et al., *Methods Enzymol.*, 144:475–489 (1987)). The peptide column may be regenerated by washing with 100 ml 8 M urea 50 mM Tris-HCl pH 7.5 followed by extensive washing with storage buffer [TBS containing 0.02% NaN$_3$].

The advantage of using peptides versus natural ligands for affinity purification of integrins is the lower cost and the potential for better purification resulting from elimination of other binding sites such as those potentially present in the type III repeat units of the fibronectin fragment previously used for the purification. Affinity purifications based on integrin antibodies have also been used (Koivunen et al., *J. Cell. Biol.*, 124:373–380 (1994)) but they are also expensive and generally do not select against inactivated integrins. Nowlin et al., *J. Biol. Chem.*, 268:20352–59 (1993) recently described a cyclic pentapeptide, RCD(ThioP)C, [SEQ ID NO: 29] which binds α$_4$β$_1$ and α$_5$β$_1$ with high affinity and demonstrated that it could be used to purify both these integrins. In contrast, the cyclic peptide CRRETAWAC [SEQ ID NO: 12] appears to be selective for α$_5$β$_1$. The usefulness of adhesive peptides for purification of integrins will likely increase as peptides with new specificities are discovered.

TABLE 1

Phage sequences bound by the α$_5$β$_1$ integrin.

| CX$_7$C library | XCRXETWXWXC library | |
|---|---|---|
| | 2nd panning | 3rd panning |
| CRRETAWAC | GCRRETEWAC | ACRRETAWAC (2) |
| CRSETYWKC | SCRRETQWHC | HCRRETAWAC |
| | VCRKETAWAC | GCRRETAWAC |
| | GCRKETAWAC | WCRRETNWAC |
| | WCRGETAWAC | SCRAETAWMC |
| | WCRPETGWRC | ACRAETAWRC |
| | | YCRPETAWAC |
| | GCREETAWQC | RCREETAWAC |
| | WCREETGWWC | RCRSETAWAC |
| | SCREETGWGC | ECRRETAWAC |
| | PCREETAWRC | ECRRETAWSC |
| | SCRDETLWWC | ECRRETAWWC |
| | RCREETLWAC | DCRRETAWRC |
| | RCRAETGWAC | DCRHETAWAC |
| | ECRRETAWGC | |
| | DCRRETSWAC | |

Two phage sequences containing the RXET motif originally isolated from the CX$_7$C library are shown. Based on the common residues in these sequences, a library displaying XCRXETXWXC peptides was constructed, where X is a variable amino acid. The library was surveyed with the α$_5$β$_1$ integrin coated on plastic with different concentrations and randomly selected clones were sequenced after the second and third round of panning.

TABLE 2

Phage sequences bound by the α$_5$β$_1$ integrin.

| CX$_5$C | CX$_6$C | CX$_9$ |
|---|---|---|
| CRGDGWC (8) | CRGDGWMC (10) | CRGDGLMCGL (2) |
| CRGDGFC (3) | CRGDGLMC (7) | CGQRGDGFCL |

TABLE 2-continued

Phage sequences bound by the α$_5$β$_1$ integrin.

| CX$_5$C | CX$_6$C | CX$_9$ |
|---|---|---|
| | CRGDGWLC (5) | CPVRRGDGWC |
| | CRGDGMWC (5) | CLRGDGLALC |
| | CRGDGMLC | CRGDGYCVFF |
| | CRGDGWIC | CWRGDHVMPC |
| | CRGDGWWC | CDWRGDNQFC |
| | CRGDGLIC | CRGDCLPTPR |
| | CRGDGLDC | |
| | CRGDGLLC | CYVNGRAWAC |
| | CRGDGLWC | CTNVNGRSAC |
| | CRGDGFLC | |
| | CRGDGQHC | CQGMHGTPAC |
| | CRGDGAFC | CGQGMHRLAC |
| | CRGDGAWC | CQGIDGTPAC |
| | CRGDNVWC | CMWLSVNYSC |
| | CRGDNAWC | CREQPASRSC |
| | CRGDAAWC | CKWRSARDLC |
| | CRGDAAHC | CVDCILRYLC |
| | CRGDRAWC | CGADSEEGPC |

A mixture of the libraries expressing CX$_5$C, CX$_6$C and CX$_9$ peptides was screened with α$_5$β$_1$. The sequences are from randomly selected clones after second, third and fourth panning. The number of clones encoding the same peptide is shown in parentheses. The RGD and NGR motifs are shown in bold.

TABLE 3

Phage sequences bound by the α$_v$β$_3$ integrin.

| CX$_5$C | CX$_6$C | CX$_7$C | CX$_9$ |
|---|---|---|---|
| CWRGDTPC | CTTRGDSFC | CARRLDAPC | CQARGDRPRC |
| CWRGDRAC | CRVRGDSWC | CPSRLDSPC | CNRRGDNWGC |
| CLRGDRVC | CLRRGDSGC | CKTPGRLDC | |
| SCRGDGRC | CISRGDTFC | CTTRSDSFC | |
| CRGDSLRC | CPSRGDALC | | |
| CRGDGRNC | CAGRGDALC | | |
| | CSPRGDAGC | CWSISPYFC | |
| | CTRRGDATC | CPDLLAQSC | |
| | CVRRGDAFC | CLVLPSTGC | |
| | CLSRGDVVC | CYSLGFLVC | |
| | CNARGDGFC | | |
| | CVTRGDHFC | | |
| | CEVRGDRIC | | |
| | CNIRGDKIC | | |
| | CNARGDKLC | | |
| | CPRGDSTLC | | |
| | CTRGDSIFC | | |
| | CTRGDSLDC | | |
| | CGRGDSHHC | | |
| | CDRGDSQSC | | |
| | CSRGDTYLC | | |
| | CLRGDIANC | | |
| | CGRGDLIHC | | |
| | CSRGDGAIC | | |
| | CFRGDDRKC | | |
| | CRGDSFVGC | | |
| | CRGDSHLQC | | |
| | CRGDNTFGC | | |
| | CRGDTVYAC | | |
| | CRGDHGTLC | | |
| | CRGDAWPGC | | |
| | CRGDLAWVC | | |
| | CRGDGIRFC | | |
| | CRGDKGWNC | | |

A pool of the CX$_5$C, CX$_6$, CX$_7$C and CX$_9$ libraries was surveyed with the integrin and randomly picked clones were sequenced. The RGD motifs are shown in bold and the RGD homologs are underlined.

TABLE 4

Phage sequences selected by $\alpha_{IIb}\beta_3$ integrin.

$\alpha_{IIb}\beta_3$

| CX$_6$C | CX$_7$C |
|---|---|
| CRGDNYWC | CRRGDFGGC |
| CRGDNSAC | CFSRGDFPC |
| CPRGDWPC | CHIRGDFPC |
| CGRGDQLC | CRYRGDLPC |
| CVRGDRMC | CYARGDYPC (2) |
| CRGDRALC | CSARGDWPC |
| CRGDTRSC | CKRGDWIRC |
| CGRGDGDC | CGARGDSRC |
| CRODVPQC | CRRMDMPDC |
| CRADVPLC | CWARRDMPC |
| CGRLDVPC | CWVRSDLGC |
| CYRRDVPC | CPLRRDWIC |
| CKGDMPRC | CTARSDRRC |
| CRHDSPRC | CMSRADRPC |
| CKRRDYPC | CSGRHDDYC (2) |
| CTRTDGWC | CHSTRDELC |
| CMRTDGRC | |
| CRTRDSPC | |
| CVVRDMPC | |

A mixture of the CX$_5$C, CX$_6$C and CX$_7$C libraries was panned with the integrin coated on plastic as described in Material and Methods. The RGD motif is shown in bold and its homologs are underlined.

TABLE 5

Phage sequences bound by the $\alpha_v\beta_5$ integrin.

| CX$_5$C CX$_6$C | CX$_7$C | CX$_9$ |
|---|---|---|
| CRGDTFC | CWTRGDSFC | CIRRGDTFGC (2) |
| CRGDVFLC | CEGRGDSFC | CQGRGDTFYC |
| | CYARGDSFC | CPRRGDTFSC |

TABLE 5-continued

Phage sequences bound by the $\alpha_v\beta_5$ integrin.

| CX$_5$C CX$_6$C | CX$_7$C | CX$_9$ |
|---|---|---|
| | CEPRGDSFC | CAHRGDTPQC |
| | CELRGDSAC | CVSRGDTPKC |
| | CLVRGDSLC | CVTRGDSFSC |
| | CHTRGDTFC | CQVRGDQFAC |
| | CISRGDTFC | CTQRGDNFFC |
| | CVVRGDTFC | CAPRGDHFAC (2) |
| | CEMRGDTFC | CQSRGDDFSC |
| | CDLRGDTYC | CGRRGDVPRC |
| | CVTRGDNFC (2) | CRGDTPGFLC |
| | VCLRGDNFC | CRGDLPRAWC |
| | CVRRGDVFC | CRGDVPAVGC |
| | CGRGDTPTC | CYRGDADFWC |
| | CRGDTYLIC | CSQKRGDTWC |
| | | CPDKRGDTYC |
| | CDCRGDCFC (2) | |
| | CDCRGDCLC (2) | CGPRERFLSC |
| | CLCRGDCIC | CIRQRIYPWC |
| | CRGDCCQSC | CGQRSSARAS |
| | | CGSPLKSIKC |
| | CLHPNVRSC | CIEIQHGKAC |
| | CDSVLRVFC | CLESRGPQKC |
| | | CRKQVMACTA |
| | | CEAKFQLHWV |
| | | CVGKELHKRV |
| | | CTRKRAVGAA |

A pool of the CX$_5$C, CX$_6$C, CX$_7$C and CX$_9$ libraries was used. The RGD motif is shown in bold. The basic residues and glutamines in the CX$_9$ non-RGD peptides are underlined.

Although the present invention has been described in detail with reference to examples above, it is understood that various modifications can be made withhout departing from the spirit of the invention. Accordingly, the invention is limited only by the following claims.

We claim:

1. A peptide that binds to $\alpha_v\beta_3$ integrin and that contains the sequence RLD in a constrained secondary conformation.

2. The peptide of claim 1, wherein the sequence RLD is contained in a nine-membered cycle.

3. The peptide of claim 3, wherein the cycle is formed from a disulfide bond, a peptide bond or a lactam bond.

4. The peptide of claim 3, wherein the sequence RLD is further contained in the sequence $CX_1X_2RLDX_3X_4C$ (SEQ ID NO: 38), wherein $X_1$, $X_2$, $X_3$ and $X_4$ are any amino acid; CARRLDAPC (SEQ ID NO: 19) or CPSRLDSPC (SEQ ID NO: 20).

5. A peptide that binds to an integrin and that contains the sequence $X_1X_2X_3RGDX_4X_5X_6$ (SEQ ID NO: 3), wherein $X_1$, $X_3$, $X_4$ and $X_6$ are involved in the formation of two bridges and $X_2$ and $X_5$ are 1 to 5 amino acids.

6. The peptide of claim 5, wherein said peptide binds to $\alpha_v\beta_3$ and $\alpha_v\beta_5$ integrins.

7. The peptide of claim 5, wherein said two bridges formed by $X_1$, $X_3$, $X_4$ and $X_6$ are disulfide bonds, peptide bonds or lactam bonds.

8. The peptide of claim 7, wherein the sequence $X_1X_2X_3RGDX_4X_5X_6$ (SEQ ID NO: 3) is $CX_2CRGDCX_5C$ (SEQ ID NO: 15), CDCRGDCFC (SEQ ID NO: 16), CDCRGDCLC (SEQ ID NO: 17), or CLCRGDCIC (SEQ ID NO: 18).

9. A method useful for attaching cells to a substrate, comprising binding a peptide of claim 5 to a substrate and contacting the substrate with the cell.

10. The method of claim 9, wherein said peptide is $CX_2CRGDCX_5C$ (SEQ ID NO: 15).

11. A patch graft, comprising a peptide of claim 5 attached to a support matrix.

12. The patch graft of claim 11, wherein the support matrix comprises collagen, glycosaminoglycan or proteoglycan.

13. The patch graft of claim 11, wherein said peptide is $CX_2CRGDCX_5C$ (SEQ ID NO: 15).

14. The patch graft of claim 13, wherein the support matrix comprises collagen, glycosaminoglycan or proteoglycan.

15. A method useful for promoting wound healing, comprising applying to the wound a patch graft of claim 11.

16. A method useful for promoting wound healing, comprising applying to the wound a patch graft of claim 13.

17. A method useful for inhibiting the attachment of osteoclasts to bone, comprising administering to an individual a peptide of claim 5.

18. The method of claim 17, wherein said peptide is $CX_2CRGDCX_5C$ (SEQ ID NO: 15).

19. A method useful for inhibiting angiogenesis, comprising administering to an individual a peptide of claim 5.

20. The method of claim 19, wherein said peptide is $CX_2CRGDCX_5C$ (SEQ ID NO: 15).

21. A method useful for inhibiting metastasis of a tumor expressing $\alpha_v\beta_3$ integrin, comprising administering to an individual a peptide of claim 5.

22. The method of claim 21, wherein said peptide is $CX_2CRGDCX_5C$ (SEQ ID NO: 15).

23. A method useful for inhibiting migration of smooth muscle cells, comprising administering to an individual a peptide of claim 5.

24. The method of claim 23, wherein said peptide is $CX_2CRGDCX_5C$ (SEQ ID NO: 15).

25. A pharmaceutical composition, comprising a peptide that binds to $\alpha_v\beta_3$ integrin and that contains the sequence RLD in a constrained secondary conformation, and a pharmaceutically-acceptable carrier therefor.

26. A pharmaceutical composition, comprising a peptide that binds to an integrin and that contains the sequence $X_1X_2X_3RGDX_4X_5X_6$ (SEQ ID NO: 3), wherein $X_1$, $X_3$, $X_4$ and $X_6$ are involved in the formation of two bridges and $X_2$ and $X_5$ are 1 to 5 amino acids.

27. A pharmaceutical composition, comprising a peptide of claim 26 that binds to $\alpha_v\beta_3$ and $\alpha_v\beta_5$ integrins, and a pharmaceutically-acceptable carrier therefor.

28. The pharmaceutical composition of claim 26, wherein said peptide is $CX_2CRGDCX_5C$ (SEQ ID NO: 15).

29. A peptide that selectively binds $\alpha_5\beta_1$ integrin and that contains the sequence RGDGX (SEQ ID NO: 2), wherein X is a tryptophan residue, wherein the sequence RGDGX (SEQ ID NO: 2) is contained in a seven-membered or nine-membered cycle, wherein the cycle is formed by a disulfide bond, a peptide bond or a lactam bond, and wherein the sequence RGDGX (SEQ ID NO: 2) is further contained in the sequence CRGDGXC (SEQ ID NO: 30).

30. The peptide of claim 8, wherein the sequence $X_1X_2X_3RGDX_4X_5X_6$ (SEQ ID NO: 3) is $CX_2CRGDCX_5C$ (SEQ ID NO: 15).

31. The peptide of claim 8, wherein the sequence $X_1X_2X_3RGDX_4X_5X_6$ (SEQ ID NO: 3) is CDCRGDCFC (SEQ ID NO: 16).

32. The peptide of claim 8, wherein the sequence $X_1X_2X_3RGDX_4X_5X_6$ (SEQ ID NO: 3) is CDCRGDCLC (SEQ ID NO: 17).

33. The peptide of claim 8, wherein the sequence $X_1X_2X_3RGDX_4X_5X_6$ (SEQ ID NO: 3) is CLCRGDCIC (SEQ ID NO: 18).

34. The pharmaceutical composition of claim 26, wherein said peptide is CDCRGDCFC (SEQ ID NO: 16).

35. The pharmaceutical composition of claim 26, wherein said peptide is CDCRGDCLC (SEQ ID NO: 17).

36. The pharmaceutical composition of claim 26, wherein said peptide is CLCRGDCIC (SEQ ID NO: 18).

* * * * *

UNITED STATES PATENT AND TRADEMARK OFFICE
CERTIFICATE OF CORRECTION

PATENT NO.    : 5,981,478
DATED         : November 9, 1999
INVENTOR(S)   : Erkki Ruoslahti and Erkki Koivunen It is certified that error appears in the above-identified patent and that said Letters Patent is hereby corrected as shown below:

Column 14,
Line 37, please delete "Bindings" and replace therefor with -- Binding --.

Column 16,
Line 23, please delete "well" and replace therefor with -- wells --.

Column 19,
Line 1, please delete "$\alpha_v\beta\beta_5$" and replace therefor with -- $\alpha_v\beta_5$ --.
Line 14, please delete "peptide" and replace therefor with -- peptides --.
Line 47, please delete "$\alpha_5\beta_1$" and replace therefor with -- $\alpha_5\beta_1$ --.

Signed and Sealed this

Ninth Day of September, 2003

JAMES E. ROGAN
*Director of the United States Patent and Trademark Office*

SEQUENCE LISTING (1) GENERAL INFORMATION:

(iii) NUMBER OF SEQUENCES: 46

(2) INFORMATION FOR SEQ ID NO:1:

(i) SEQUENCE CHARACTERISTICS:
      (A) LENGTH: 7 amino acids
      (B) TYPE: amino acid
      (D) TOPOLOGY: both (xi) SEQUENCE DESCRIPTION: SEQ ID NO:1:

Arg Xaa Glu Thr Xaa Trp Xaa
1              5

(2) INFORMATION FOR SEQ ID NO:2:

(i) SEQUENCE CHARACTERISTICS:
      (A) LENGTH: 5 amino acids
      (B) TYPE: amino acid
      (D) TOPOLOGY: both (ix) FEATURE:
      (A) NAME/KEY: Peptide
      (B) LOCATION: 5
      (D) OTHER INFORMATION: /note= "Xaa = an amino acid with a
          hydrophobic, aromatic side chain."

(xi) SEQUENCE DESCRIPTION: SEQ ID NO:2:

Arg Gly Asp Gly Xaa
1               5

(2) INFORMATION FOR SEQ ID NO:3:

(i) SEQUENCE CHARACTERISTICS:
        (A) LENGTH: 9 amino acids
        (B) TYPE: amino acid
        (D) TOPOLOGY: circular (ix) FEATURE:
        (A) NAME/KEY: Peptide
        (B) LOCATION: 1
        (D) OTHER INFORMATION: /note= "Xaa = residue capable of
            forming a cyclizing bond."

(ix) FEATURE:
        (A) NAME/KEY: Peptide
        (B) LOCATION: 3
        (D) OTHER INFORMATION: /note= "Xaa = residue capable of
            forming a cyclizing bond."

(ix) FEATURE:
        (A) NAME/KEY: Peptide
        (B) LOCATION: 7
        (D) OTHER INFORMATION: /note= "Xaa = residue capable of
            forming a cyclizing bond."

(ix) FEATURE:
        (A) NAME/KEY: Peptide
        (B) LOCATION: 9
        (D) OTHER INFORMATION: /note= "Xaa = residue capable of
            forming a cyclizing bond."

(ix) FEATURE:
        (A) NAME/KEY: Peptide
        (B) LOCATION: 2
        (D) OTHER INFORMATION: /note= "Xaa = 1 to 5 amino acids."

(ix) FEATURE:
        (A) NAME/KEY: Peptide
        (B) LOCATION: 8
        (D) OTHER INFORMATION: /note= "Xaa = 1 to 5 amino acids."

(xi) SEQUENCE DESCRIPTION: SEQ ID NO:3:

Xaa Xaa Xaa Arg Gly Asp Xaa Xaa Xaa
1               5

(2) INFORMATION FOR SEQ ID NO:4:

(i) SEQUENCE CHARACTERISTICS:
        (A) LENGTH: 7 amino acids
        (B) TYPE: amino acid
        (D) TOPOLOGY: both (xi) SEQUENCE DESCRIPTION: SEQ ID NO:4:

Glu Leu Arg Gly Asp Gly Trp
1               5

(2) INFORMATION FOR SEQ ID NO:5:

(i) SEQUENCE CHARACTERISTICS:
        (A) LENGTH: 10 amino acids
        (B) TYPE: amino acid
        (D) TOPOLOGY: circular (xi) SEQUENCE DESCRIPTION: SEQ ID NO:5:

Gly Ala Cys Arg Gly Asp Cys Leu Gly Ala
1               5                   10

(2) INFORMATION FOR SEQ ID NO:6:

(i) SEQUENCE CHARACTERISTICS:
        (A) LENGTH: 13 amino acids
        (B) TYPE: amino acid
        (D) TOPOLOGY: circular (xi) SEQUENCE DESCRIPTION: SEQ ID NO:6:

Gly Ala Cys Arg Arg Glu Thr Ala Trp Ala Cys Gly Ala
1               5                   10

(2) INFORMATION FOR SEQ ID NO:7:

(i) SEQUENCE CHARACTERISTICS:
        (A) LENGTH: 6 amino acids
        (B) TYPE: amino acid
        (D) TOPOLOGY: circular (xi) SEQUENCE DESCRIPTION: SEQ ID NO:7:

Cys Arg Gly Asp Cys Leu
1               5

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: both (xi) SEQUENCE DESCRIPTION: SEQ ID NO:8:

Arg Arg Glu Thr Ala Trp Ala
1               5

(2) INFORMATION FOR SEQ ID NO:9:

(i) SEQUENCE CHARACTERISTICS:
        (A) LENGTH: 5 amino acids
        (B) TYPE: amino acid
        (D) TOPOLOGY: both (xi) SEQUENCE DESCRIPTION: SEQ ID NO:9:

Arg Gly Asp Gly Trp
1               5

(2) INFORMATION FOR SEQ ID NO:10:

(i) SEQUENCE CHARACTERISTICS:
        (A) LENGTH: 11 amino acids
        (B) TYPE: amino acid
        (D) TOPOLOGY: circular (xi) SEQUENCE DESCRIPTION: SEQ ID NO:10:

Ala Cys Asp Cys Arg Gly Asp Cys Phe Cys Gly
1               5                   10

(2) INFORMATION FOR SEQ ID NO:11:

(i) SEQUENCE CHARACTERISTICS:
        (A) LENGTH: 9 amino acids
        (B) TYPE: amino acid
        (D) TOPOLOGY: circular (xi) SEQUENCE DESCRIPTION: SEQ ID NO:11:

Cys Arg Xaa Glu Thr Xaa Trp Xaa Cys
1               5

(2) INFORMATION FOR SEQ ID NO:12:

(i) SEQUENCE CHARACTERISTICS:
    (A) LENGTH: 9 amino acids
    (B) TYPE: amino acid
    (D) TOPOLOGY: circular (xi) SEQUENCE DESCRIPTION: SEQ ID NO:12:

Cys Arg Arg Glu Thr Ala Trp Ala Cys
1               5

(2) INFORMATION FOR SEQ ID NO:13:

(i) SEQUENCE CHARACTERISTICS:
        (A) LENGTH: 7 amino acids
        (B) TYPE: amino acid
        (D) TOPOLOGY: circular (xi) SEQUENCE DESCRIPTION: SEQ ID NO:13:

Cys Arg Gly Asp Gly Trp Cys
1               5

(2) INFORMATION FOR SEQ ID NO:14:

(i) SEQUENCE CHARACTERISTICS:
        (A) LENGTH: 7 amino acids
        (B) TYPE: amino acid
        (D) TOPOLOGY: circular (xi) SEQUENCE DESCRIPTION: SEQ ID NO:14:

Cys Arg Gly Asp Gly Phe Cys
1               5

(2) INFORMATION FOR SEQ ID NO:15:

(i) SEQUENCE CHARACTERISTICS:
        (A) LENGTH: 9 amino acids
        (B) TYPE: amino acid
        (D) TOPOLOGY: circular (xi) SEQUENCE DESCRIPTION: SEQ ID NO:15:

Cys Xaa Cys Arg Gly Asp Cys Xaa Cys
1               5

(2) INFORMATION FOR SEQ ID NO:16:

(i) SEQUENCE CHARACTERISTICS:
        (A) LENGTH: 9 amino acids
        (B) TYPE: amino acid
        (D) TOPOLOGY: circular (xi) SEQUENCE DESCRIPTION: SEQ ID NO:16:

Cys Asp Cys Arg Gly Asp Cys Phe Cys
1               5

(2) INFORMATION FOR SEQ ID NO:17:

(i) SEQUENCE CHARACTERISTICS:
        (A) LENGTH: 9 amino acids
        (B) TYPE: amino acid
        (D) TOPOLOGY: circular (xi) SEQUENCE DESCRIPTION: SEQ ID NO:17:

Cys Asp Cys Arg Gly Asp Cys Leu Cys
1               5

(2) INFORMATION FOR SEQ ID NO:18:

(i) SEQUENCE CHARACTERISTICS:
        (A) LENGTH: 9 amino acids (B) TYPE: amino acid
            (D) TOPOLOGY: circular (xi) SEQUENCE DESCRIPTION: SEQ ID NO:18:

Cys Leu Cys Arg Gly Asp Cys Ile Cys
1               5

(2) INFORMATION FOR SEQ ID NO:19:

(i) SEQUENCE CHARACTERISTICS:
            (A) LENGTH: 9 amino acids
            (B) TYPE: amino acid
            (D) TOPOLOGY: circular (xi) SEQUENCE DESCRIPTION: SEQ ID NO:19:

Cys Ala Arg Arg Leu Asp Ala Pro Cys
1               5

(2) INFORMATION FOR SEQ ID NO:20:

(i) SEQUENCE CHARACTERISTICS:
            (A) LENGTH: 9 amino acids
            (B) TYPE: amino acid
            (D) TOPOLOGY: circular (xi) SEQUENCE DESCRIPTION: SEQ ID NO:20:

Cys Pro Ser Arg Leu Asp Ser Pro Cys
1               5

(2) INFORMATION FOR SEQ ID NO:21:

(i) SEQUENCE CHARACTERISTICS:
            (A) LENGTH: 6 amino acids
            (B) TYPE: amino acid
            (D) TOPOLOGY: linear (xi) SEQUENCE DESCRIPTION: SEQ ID NO:21:

Gly Arg Gly Asp Ser Pro
1               5

(2) INFORMATION FOR SEQ ID NO:22:

(i) SEQUENCE CHARACTERISTICS:
            (A) LENGTH: 7 amino acids
            (B) TYPE: amino acid
            (D) TOPOLOGY: linear (xi) SEQUENCE DESCRIPTION: SEQ ID NO:22:

Gly Arg Gly Asp Ser Pro Lys
1               5

(2) INFORMATION FOR SEQ ID NO:23:

(i) SEQUENCE CHARACTERISTICS:
            (A) LENGTH: 6 amino acids
            (B) TYPE: amino acid
            (D) TOPOLOGY: linear (xi) SEQUENCE DESCRIPTION: SEQ ID NO:23:

Gly Arg Gly Glu Ser Pro
1               5

(2) INFORMATION FOR SEQ ID NO:24:

(i) SEQUENCE CHARACTERISTICS:
            (A) LENGTH: 9 amino acids
            (B) TYPE: amino acid
            (D) TOPOLOGY: circular (xi) SEQUENCE DESCRIPTION: SEQ ID NO:24:

Cys Glu Leu Arg Gly Asp Gly Trp Cys
1               5

(2) INFORMATION FOR SEQ ID NO:25:

(i) SEQUENCE CHARACTERISTICS:
        (A) LENGTH: 9 amino acids
        (B) TYPE: amino acid
        (D) TOPOLOGY: circular (xi) SEQUENCE DESCRIPTION: SEQ ID NO:25:

Cys Arg Ser Glu Thr Tyr Trp Lys Cys
1               5

(2) INFORMATION FOR SEQ ID NO:26:

(i) SEQUENCE CHARACTERISTICS:
        (A) LENGTH: 10 amino acids
        (B) TYPE: amino acid
        (D) TOPOLOGY: both (xi) SEQUENCE DESCRIPTION: SEQ ID NO:26:

Xaa Cys Arg Xaa Glu Thr Xaa Trp Xaa Cys
1               5                   10

(2) INFORMATION FOR SEQ ID NO:27:

(i) SEQUENCE CHARACTERISTICS:
        (A) LENGTH: 8 amino acids
        (B) TYPE: amino acid
        (D) TOPOLOGY: circular (xi) SEQUENCE DESCRIPTION: SEQ ID NO:27:

Cys Arg Gly Asp Gly Trp Met Cys
1               5

(2) INFORMATION FOR SEQ ID NO:28:

(i) SEQUENCE CHARACTERISTICS:
        (A) LENGTH: 6 amino acids
        (B) TYPE: amino acid
        (D) TOPOLOGY: both (xi) SEQUENCE DESCRIPTION: SEQ ID NO:28:

Asn Gly Arg Ala His Ala
1               5

(2) INFORMATION FOR SEQ ID NO:29:

(i) SEQUENCE CHARACTERISTICS:
        (A) LENGTH: 5 amino acids
        (B) TYPE: amino acid
        (D) TOPOLOGY: circular (ix) FEATURE:
        (A) NAME/KEY: Peptide
        (B) LOCATION: 4
        (D) OTHER INFORMATION: /note= "Xaa = (ThioP)"

(xi) SEQUENCE DESCRIPTION: SEQ ID NO:29:

Arg Cys Asp Xaa Cys
1               5

(2) INFORMATION FOR SEQ ID NO:30:

(i) SEQUENCE CHARACTERISTICS:

(A) LENGTH: 7 amino acids
                    (B) TYPE: amino acid
                    (D) TOPOLOGY: circular (ix) FEATURE:
                    (A) NAME/KEY: Peptide
                    (B) LOCATION: 6
                    (D) OTHER INFORMATION: /note= "Xaa = hydrophobic, aromatic
                        amino acid."

(xi) SEQUENCE DESCRIPTION: SEQ ID NO:30:

Cys Arg Gly Asp Gly Xaa Cys
1               5

(2) INFORMATION FOR SEQ ID NO:31:

(i) SEQUENCE CHARACTERISTICS:
                    (A) LENGTH: 5 amino acids
                    (B) TYPE: amino acid
                    (D) TOPOLOGY: both (xi) SEQUENCE DESCRIPTION: SEQ ID NO:31:

Arg Gly Asp Ser Phe
1               5

(2) INFORMATION FOR SEQ ID NO:32:

(i) SEQUENCE CHARACTERISTICS:
                    (A) LENGTH: 5 amino acids
                    (B) TYPE: amino acid
                    (D) TOPOLOGY: both (xi) SEQUENCE DESCRIPTION: SEQ ID NO:32:

Arg Gly Asp Thr Phe
1               5

(2) INFORMATION FOR SEQ ID NO:33:

(i) SEQUENCE CHARACTERISTICS:
                    (A) LENGTH: 9 amino acids
                    (B) TYPE: amino acid
                    (D) TOPOLOGY: circular (xi) SEQUENCE DESCRIPTION: SEQ ID NO:33:

Cys Arg Gly Asp Cys Cys Xaa Xaa Cys
1               5

(2) INFORMATION FOR SEQ ID NO:34:

(i) SEQUENCE CHARACTERISTICS:
                    (A) LENGTH: 9 amino acids
                    (B) TYPE: amino acid
                    (D) TOPOLOGY: circular (xi) SEQUENCE DESCRIPTION: SEQ ID NO:34:

Ala Cys Arg Gly Asp Gly Trp Cys Gly
1               5

(2) INFORMATION FOR SEQ ID NO:35:

(i) SEQUENCE CHARACTERISTICS:
                    (A) LENGTH: 11 amino acids
                    (B) TYPE: amino acid
                    (D) TOPOLOGY: circular (xi) SEQUENCE DESCRIPTION: SEQ ID NO:35:

Ala Cys Pro Ser Arg Leu Asp Ser Pro Cys Gly
1               5                  10

(2) INFORMATION FOR SEQ ID NO:36:

(i) SEQUENCE CHARACTERISTICS:
        (A) LENGTH: 13 amino acids
        (B) TYPE: amino acid
        (D) TOPOLOGY: circular (xi) SEQUENCE DESCRIPTION: SEQ ID NO:36:

Gly Ala Cys Glu Leu Arg Gly Asp Gly Trp Cys Gly Ala
1         5                 10

(2) INFORMATION FOR SEQ ID NO:37:

(i) SEQUENCE CHARACTERISTICS:
        (A) LENGTH: 5 amino acids
        (B) TYPE: amino acid
        (D) TOPOLOGY: circular (xi) SEQUENCE DESCRIPTION: SEQ ID NO:37:

Cys Arg Gly Asp Cys
1         5

(2) INFORMATION FOR SEQ ID NO:38:

(i) SEQUENCE CHARACTERISTICS:
        (A) LENGTH: 9 amino acids
        (B) TYPE: amino acid
        (D) TOPOLOGY: circular (xi) SEQUENCE DESCRIPTION: SEQ ID NO:38:

Cys Xaa Xaa Arg Leu Asp Xaa Xaa Cys
1         5

(2) INFORMATION FOR SEQ ID NO:39:

(i) SEQUENCE CHARACTERISTICS:
        (A) LENGTH: 7 amino acids
        (B) TYPE: amino acid
        (D) TOPOLOGY: circular (xi) SEQUENCE DESCRIPTION: SEQ ID NO:39:

Cys Xaa Xaa Xaa Xaa Xaa Cys
1         5

(2) INFORMATION FOR SEQ ID NO:40:

(i) SEQUENCE CHARACTERISTICS:
        (A) LENGTH: 8 amino acids
        (B) TYPE: amino acid
        (D) TOPOLOGY: circular (xi) SEQUENCE DESCRIPTION: SEQ ID NO:40:

Cys Xaa Xaa Xaa Xaa Xaa Xaa Cys
1         5

(2) INFORMATION FOR SEQ ID NO:41:

(i) SEQUENCE CHARACTERISTICS:
        (A) LENGTH: 9 amino acids
        (B) TYPE: amino acid
        (D) TOPOLOGY: circular (xi) SEQUENCE DESCRIPTION: SEQ ID NO:41:

Cys Xaa Xaa Xaa Xaa Xaa Xaa Xaa Cys
1         5

(2) INFORMATION FOR SEQ ID NO:42:

(i) SEQUENCE CHARACTERISTICS:
            (A) LENGTH: 10 amino acids
            (B) TYPE: amino acid
            (D) TOPOLOGY: both (xi) SEQUENCE DESCRIPTION: SEQ ID NO:42:

Cys Xaa Xaa Xaa Xaa Xaa Xaa Xaa Xaa Xaa
1               5                   10

(2) INFORMATION FOR SEQ ID NO:43:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ix) FEATURE:
            (A) NAME/KEY: repeat_region
            (B) LOCATION: 4..18
            (D) OTHER INFORMATION: /note= "N = equal molar mixture of
                A, C, G, T; K = G or T."

(xi) SEQUENCE DESCRIPTION: SEQ ID NO:43:

TGTNNKNNKN NKNNKNNKTG T                                                  21

(2) INFORMATION FOR SEQ ID NO:44:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ix) FEATURE:
            (A) NAME/KEY: repeat_region
            (B) LOCATION: 4..21
            (D) OTHER INFORMATION: /note= "N = equal molar mixture of
                A, C, G, T; K = G or T."

(xi) SEQUENCE DESCRIPTION: SEQ ID NO:44:

TGTNNKNNKN NKNNKNNKNN KTGT                                               24

(2) INFORMATION FOR SEQ ID NO:45:

(i) SEQUENCE CHARACTERISTICS:
            (A) LENGTH: 27 base pairs
            (B) TYPE: nucleic acid
            (C) STRANDEDNESS: single
            (D) TOPOLOGY: linear (ix) FEATURE:
            (A) NAME/KEY: repeat_region
            (B) LOCATION: 4..24
            (D) OTHER INFORMATION: /note= "N = equal molar mixture of
                A, C, G, T; K = G or T."

(xi) SEQUENCE DESCRIPTION: SEQ ID NO:45:

TGTNNKNNKN NKNNKNNKNN KNNKTGT                                            27

(2) INFORMATION FOR SEQ ID NO:46:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ix) FEATURE:
            (A) NAME/KEY: repeat_region
            (B) LOCATION: 4..30

-continued (D) OTHER INFORMATION: /note= "N = equal molar mixture of
    A, C, G, T; K = G or T."

(xi) SEQUENCE DESCRIPTION: SEQ ID NO:46:

TGTNNKNNKN NKNNKNNKNN KNNKNNKNNK    30